(12) United States Patent
Chen

(10) Patent No.: US 11,708,595 B2
(45) Date of Patent: Jul. 25, 2023

(54) NANOSTRUCTURED BIOMIMETIC PROTEIN SUPERCONDUCTIVE DEVICES OF MAKING AND ITS MULTIPLE APPLICATIONS THERETO

(71) Applicant: Ellen Tuanying Chen, Rockville, MD (US)

(72) Inventor: Ellen Tuanying Chen, Rockville, MD (US)

( * ) Notice: Subject to any disclaimer, the term of this patent is extended or adjusted under 35 U.S.C. 154(b) by 725 days.

(21) Appl. No.: 16/742,745

(22) Filed: Jan. 14, 2020

(65) Prior Publication Data

US 2020/0362384 A1  Nov. 19, 2020

Related U.S. Application Data

(60) Provisional application No. 62/848,422, filed on May 15, 2019.

(51) Int. Cl.
| | |
|---|---|
| *G06N 10/40* | (2022.01) |
| *C12Q 1/00* | (2006.01) |
| *G01N 27/414* | (2006.01) |
| *G01N 33/543* | (2006.01) |
| *G01N 27/327* | (2006.01) |
| *H10N 60/12* | (2023.01) |
| *H10N 60/00* | (2023.01) |
| *H10N 60/80* | (2023.01) |
| *H10N 60/85* | (2023.01) |
| *H10N 69/00* | (2023.01) |
| *B82Y 5/00* | (2011.01) |

(52) U.S. Cl.
CPC .......... *C12Q 1/002* (2013.01); *G01N 27/3278* (2013.01); *G01N 27/4145* (2013.01); *G01N 27/4146* (2013.01); *G01N 33/5438* (2013.01); *H10N 60/12* (2023.02); *H10N 60/805* (2023.02); *H10N 60/851* (2023.02); *H10N 60/99* (2023.02); *H10N 69/00* (2023.02); *B82Y 5/00* (2013.01)

(58) Field of Classification Search
CPC ............... C12Q 1/002; G01N 27/3278; G01N 27/4145; G01N 33/5438; H01L 27/18; H01L 39/005; H01L 39/121; B82Y 5/00
See application file for complete search history.

(56) References Cited

U.S. PATENT DOCUMENTS 11,079,354 B2 * 8/2021 Chen ...................... G01N 27/27

* cited by examiner

*Primary Examiner* — Quan Tra

(57) ABSTRACT

A multiple functioning superconductive device was invented based on Toroidal Josephson Junction (FFTJJ) array with 3D-cage structure self-assembled organo-metallic superlattice membrane. The device not only mimics the structure and function of an activated Matrix Metalloproteinase-2 (MMP-2) protein, but also mimics the cylinder structure of the Heat Shock Protein (HSP60) protein, that works at room temperature under a normal atmosphere, and without external electromagnetic power applied. The device enabled direct rapid real-time monitoring atto-molarity concentration ATP in biological specimens and was able to define the anti-inflammatory and pro-inflammatory status revealed a transitional range of ATP concentration under antibody-free, tracer-free and label-free conditions.

16 Claims, 35 Drawing Sheets

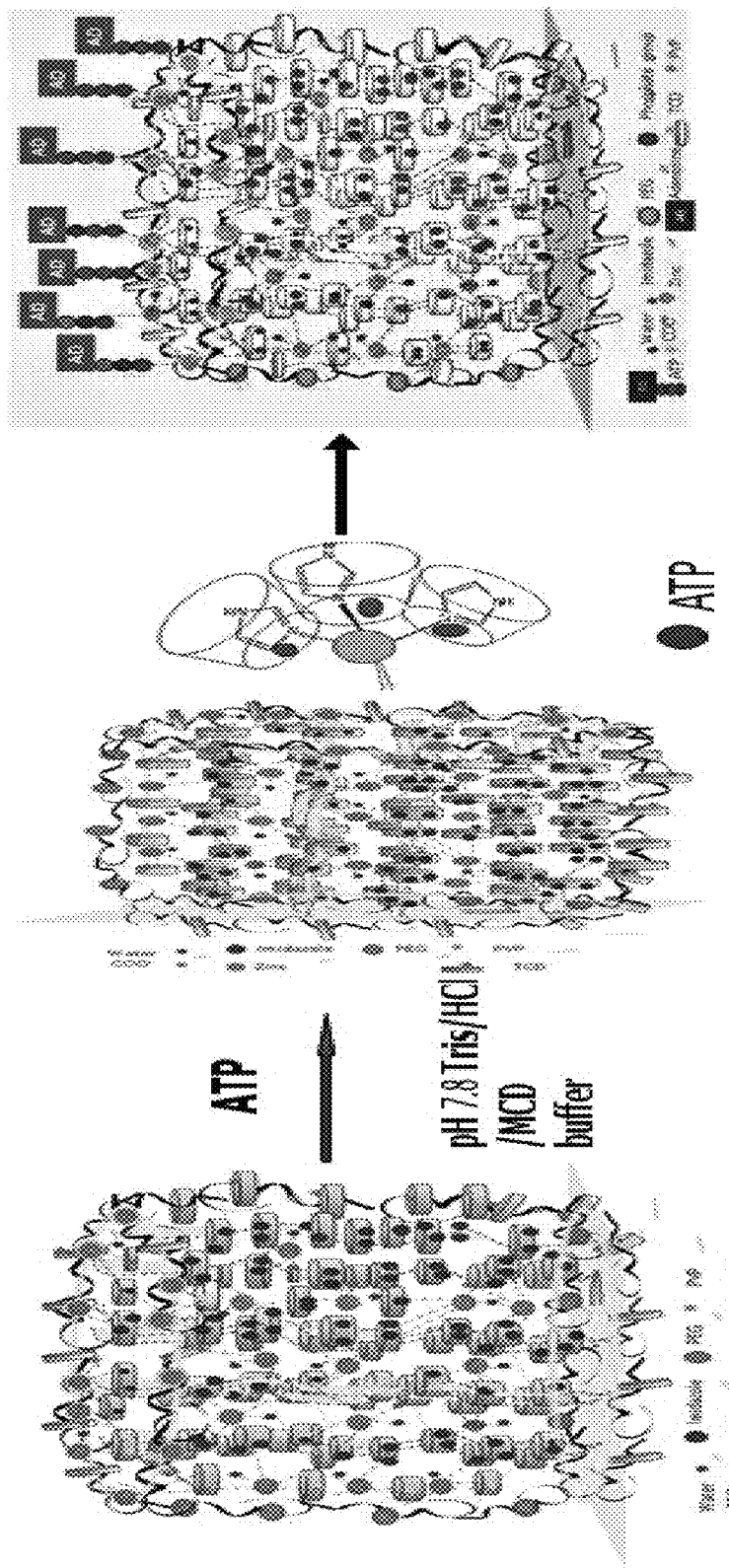

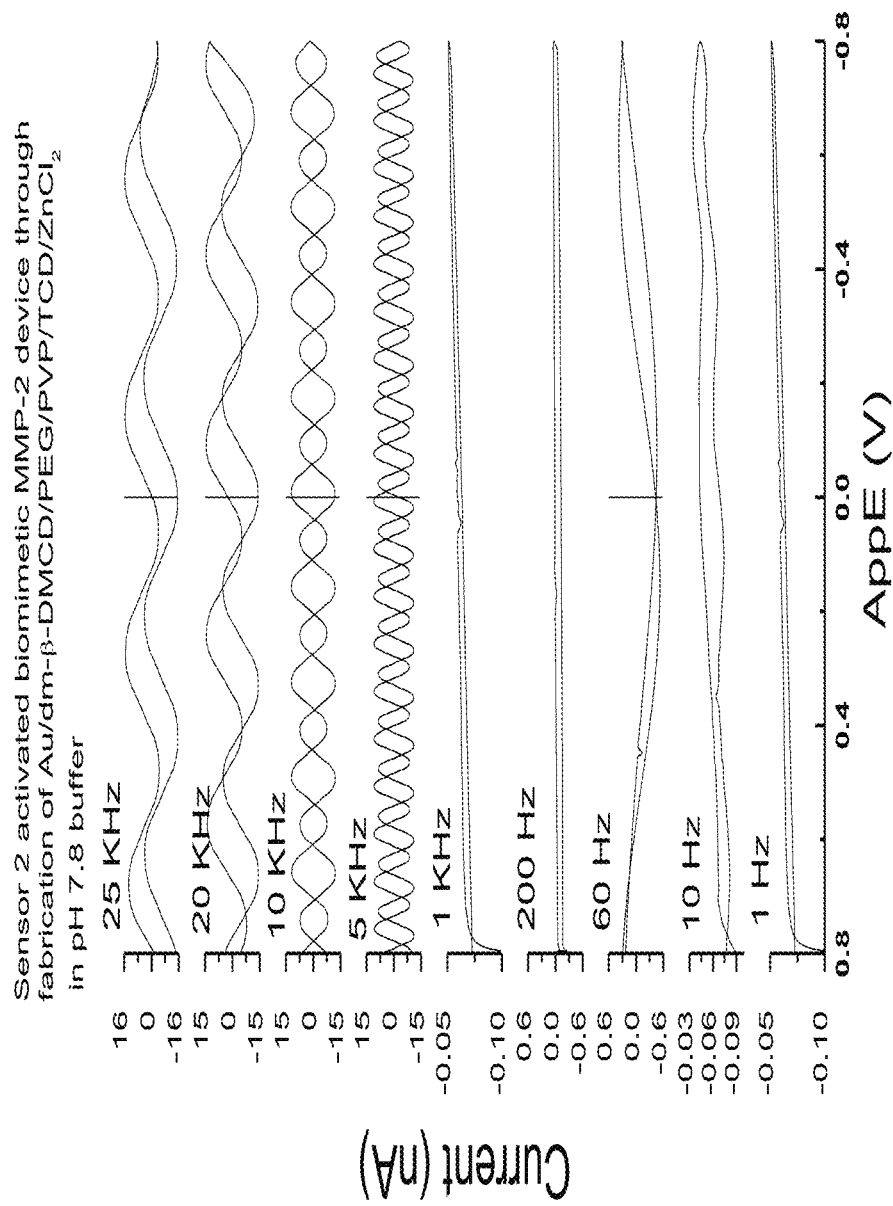

Sensor 2's i-V curves at zero-bias potential for with ATP from 25 aM to 2 µM compared with the control at 60 Hz scan rate in the tris/MCD media.

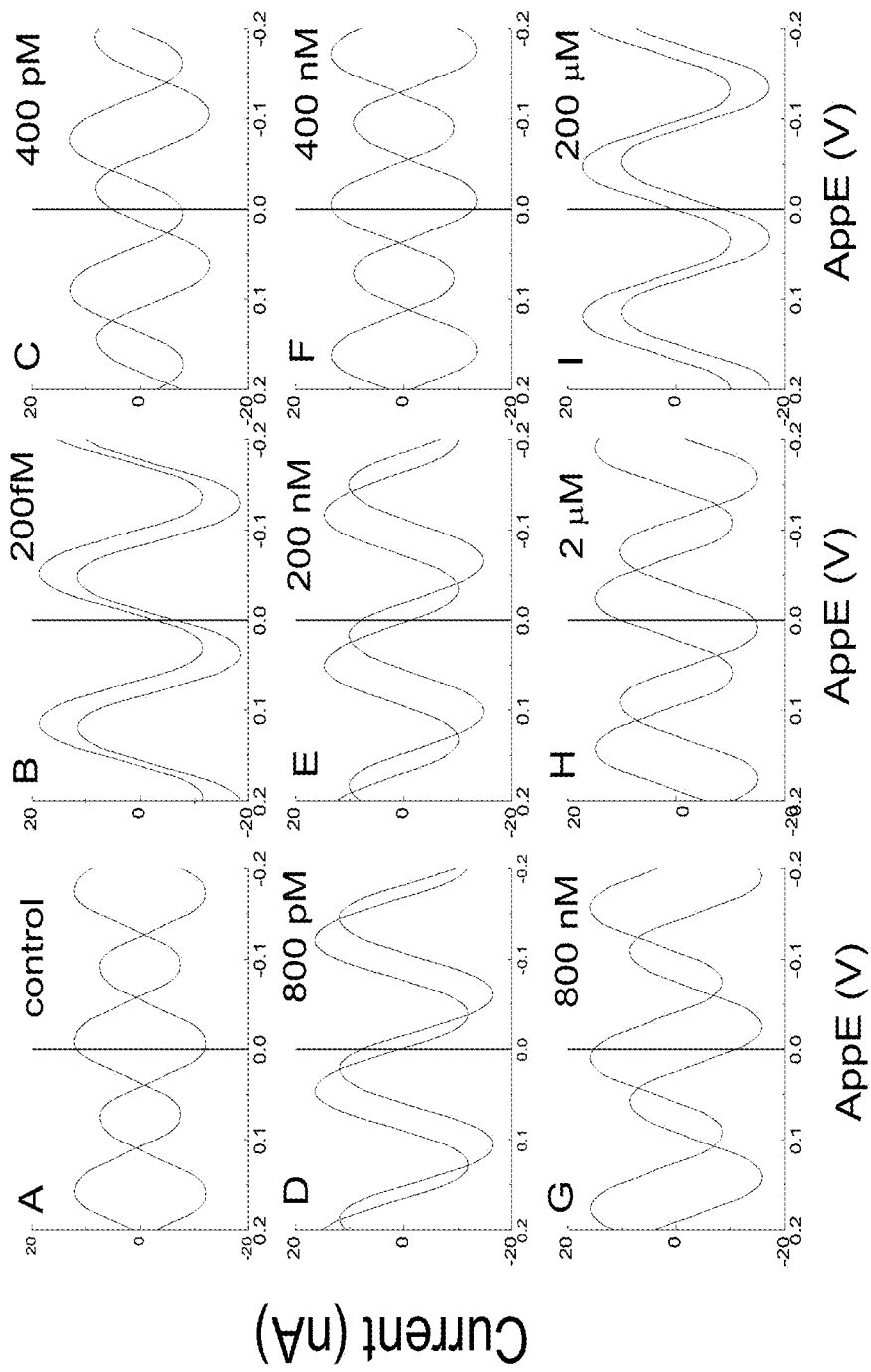

ATP effects on sensor's Josephson Supercurrent and pahse at zero-bias in 10 consecutive cycles at scan rate 60 Hz

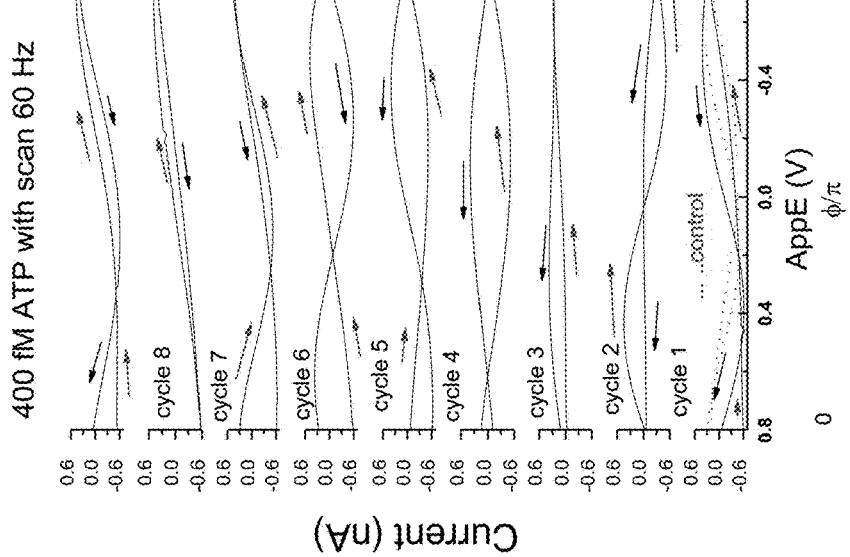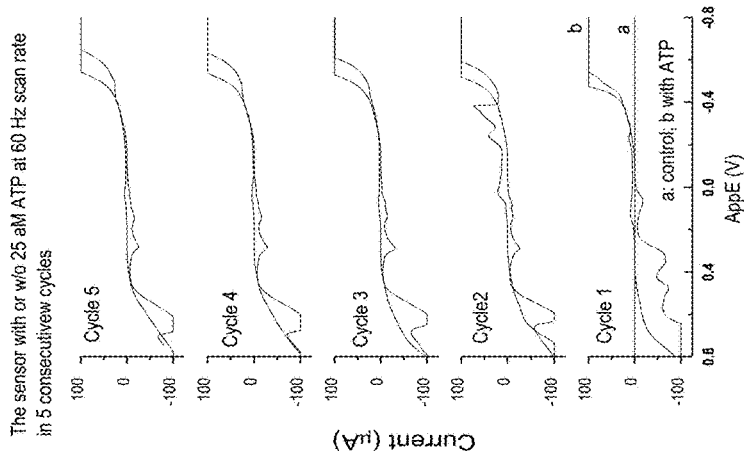
Fig. 12A  Fig. 12B  Fig. 12C

Fig. 22D

Table 1. Comparison of the Method Performance for Quantitation of ATP Spiked in the Milk Samples using the voltage method.

| ATP Recovery (% (sd)) | | | | HSP60-effect (% (sd)) | Sample type |
|---|---|---|---|---|---|
| Without LPS | | With LPS challenge | | | |
| Low ATP 100 aM | High ATP 60 nM | Low LPS 10 fg/mL | High LPS 90 fg/mL | | |
| 98.6 (1.0) | 96.5 (0.14) | 103 (0.8) | 103 (0.7) | 0 (0.3) | HK |
| 98.6 (0.8) | 96.8 (2.0) | 97.0 (1.0) | 18.8 (0.3) | 0 (0.2) | OK |

For with LPS, ATP=60 nM. The whole cell voltage data were used. HK: human milk; OK refers to the organic milk samples.

NANOSTRUCTURED BIOMIMETIC PROTEIN SUPERCONDUCTIVE DEVICES OF MAKING AND ITS MULTIPLE APPLICATIONS THERETO

CROSS-REFERENCE TO RELATED APPLICATIONS

This patent application is a U.S. Non-Provisional Patent Application in the title of Nanostructured Biomimetic Superconductive Devices of Making and Its Multiple Applications Thereto, that claims the benefit of the U.S. provisional patent application No. 62/848,422, in the title Nanostructured Biomimetic Organo-metallic Superconductive Devices of Making and its applications for Direct Real-time Monitoring Atto-Molarity ATP in Biological Specimens" filed on May 15, 2019. The entire disclosure of the prior Patent Application Ser. No. 62/848,422 is hereby incorporated by reference, as is set forth herein in its entirety.

FIELD OF THE INVENTION

The present invention relates to the field of applications in the superconductor, in particular, to a device having both characteristics in superconductivity and memristive/memcapacitive/meminductive embedded with non-ferromagnetic switches functioning at room temperature and its applications in sensing biological specimens.

BACKGROUND OF THE INVENTION

Real-time monitoring of ATP in biological specimens is a convenient means to monitor hygiene in healthcare units and for medical devices. Rapid and precise monitoring has been in strong demand from the public and under tight regulations [1-8].

Researchers found a rapid measurement of ATP in a series of diluted bacterial cultures correlates with the bacterial concentrations contaminated in the biological specimens, thus ATP testing becomes an important indicator for monitoring hygiene in healthcare units [9-11].

The predominate luciferase bioluminescent sensor method, the fluorescence in situ hybridization (FISH) method, the HPLC method, the flow cytometry method, and the immobilized gene electrochemical sensor method are common methods for ATP [7-14]. Among these methods, the luciferase bioluminescent sensor method has been recommended by CDC for assessing hospital device surface hygiene and has been used for decades. Nante's review article revealed the ATP luciferase bioluminescent portable sensor method is not a standardized methodology, because each tool has different benchmark values, not always clearly defined. The authors stressed this technique could be used to assess, in real-time, hospital surfaces' cleanliness, but has its limitations of not accurate in detecting bacteria, and the requirement of the washing out of the disinfectant step on the surfaces before testing are drawbacks [14]. The gene method could improve the detection limits to 10 fM ATP, but it is not real-time monitoring and the procedures are burdensome [12]. Even NASA recently recognized an unmet need for real-time online assessing the drinking water contamination for astronauts who are on their space flight, because all current methods used for monitoring water quality including the ATP bioluminescent and gene methods were deemed unfit because the requirements of (1) rapid accurate reagent-free real-time testing; (2) the testing machine needs to be lightweight and small in size; (3) there should be no sample preparation steps, have not met [15]. In the face of the demand and challenges, our group proposed an innovative approach to attack the problems, that is to develop superlattice nanostructured superconductive/memristive sensors having organo-metallic crossed-linking polymer membranes which work at Josephson Junction at the zero-bias potential, may overcome protein nonspecific bounding and increase accuracy, based upon our prior experience using the superconductive/memristive device to enable direct detection of collagen-1 in 16.7 atto molarities with higher than 96% accuracy using fresh human capillary blood serum specimens at low (8.3 fM) and high (0.55 nM) levels having imprecision of 4.9% and 0.8%, respectively compared with the controls, under antibody-free, tracer-free, and reagent-free conditions at room temperature [16-17].

Recent theoretical predictions of Josephson-based meminductive and memristive quantum superconducting devices not only have multiple state superposition properties but also the Cooper-pair waves behave hysterically have drawn attention [18-20]. Herein by utilizing these properties, we assert that significantly improving the ATP testing method may be accomplishable. We planned to develop two types of sensors, namely, the biomimetic matrix metalloproteinase (vTMP-2) Sensor 1 at its active state by a heating method to switch "Off" the cysteine group in the membrane, which is ready for biocommunication with ATP; then the results due to ATP's interaction will be compared with Sensor 2, also at its active state of the biomimetic MMP-2, but by a direct fabrication method of organo-metallic self-assembled cross-linked polymer without cysteine. It is well-known that superlattice membranes have been used as candidates for applications in superconductivity [21].

Literature reported ATP hydrolyzation extracellularly induces cancer cells' drug resistance [22-25]. Assessing human milk's immunological advantage over cow milk in preventing extracellular ATP hydrolyzation is important to human health. Shonhai's group published a review article regarding the roles of the Heat Shock Proteins (HSP) that acted as immunomodulates whose capability is to transform the anti-inflammatory property when the LiSP concentrations are low to the pro-inflammatory property when HSP concentrations are high [26], and unfortunately, the authors did not define the concentration range. We felt an unmet need exists for this health-related important topic. Extracellular ATP concentration and intracellular ATP concentration ranges are important related to HSPs' functions either in physiological or pathological function, because HSPs primarily occur extracellularly, but also reported from literature, HSPs occur in an intracellular micro-environment [27]. If we can build a well-characterized and well-controlled system to define the critical HSP concentration ranges in the transformation between the two statuses that would be a primary attempt toward a resolution.

SUMMARY OF THE INVENTION

It is an object of the present invention to provide a new generation of organo-metallic superconductive, memristive/memcapacitive device compromising of the active sites of a biomimetic Matrix Metalloproteinase (MMP-2) in the membrane of the device.

It is an object of the present invention to provide a new generation of organo-metallic superconductor/memristor/memcapacitor with multiple-layer curvature structure mimicking the function and structure of cation-diffusive facilitator (CDF) protein YiiP of *E. coli* (gram-negative), and to efflux zinc ions from cellular membrane.

It is an object of the present invention to further provide the biomimetic YiiP protein which is capable to be a periplasmic zinc chaperone for providing zinc to *E. coli* when it is in a starvation zinc state.

It is a further object of the present invention to provide the biomimetic YiiP protein which is capable to be a Heat Shock Protein (HSP60) chaperone of GroEL in helping folding of a protein in its cavity.

It is a further object of the present invention to provide the biomimetic MMP-2 sensor which is able to sense aM ATP concentration presence in biological samples in a direct, rapid real-time monitoring fashion of hospital instrumental hygiene without using an antibody, labeling, and other burdensome procedures.

It is a further object of the present invention to provide the biomimetic MMP-2 sensor which is able to be memory storage and a superlattice quantum computing chip working at room temperature.

It is a further object of the present invention to provide a method that can be optimally operated for fabrication of the self-assembled 3D-nanocage structure multiple-layer membrane on an electrode surface acted as a living biological cell model to assess the immunomodulant concentration effect.

It is a further object of the present invention to provide a device having multiple utilities, not only in sensing multiple analytes, but also can be used for defining the immunomodulant concentration effect on transformations from an anti-inflammatory to a pro-inflammatory status in the presence of LPS challenge with a wide range ATP concentration change in the biological specimens.

It is a further object of the present invention to provide a device to direct monitor the reversible membrane potential change under the influence of ATP concentrations.

BRIEF DESCRIPTION OF THE DRAWINGS

FIG. 4 illustrates the scheme of the steps of direct detection of ATP using the 3D-nanocage structure biomimetic MMP-2 membrane sensor/superconductor approach.

Step 1: The Direct Electron-relay (DER) model of the 3D-nanocage polymer network structure between the zinc ions from the activated biomimetic MMIP-2, by elimination of the cysteine group from the polymer mixture of triacetyl-β-cyclodextrin (TCD), polyethylene glycol diglycidyl ether (PEG), poly(4-vinyl pyridine) (PVP), bis-substituted imidazole dimethyl-β-cyclodextrin (bM-β-DMCD), cysteine and embedded zinc chloride in appropriate proportions before deposited on the gold chip, and the mM-β-DMCD (short names as MCD) in Tris/HCl buffer. Step 2: Form a long-range DET in the presence of Tris/MCD media with ATP being included in the cyclodextrin cavities, that not only stabilized ATP but also invited ATP to participate in the long-range direct electron-relay chain between the media and the 3D-nanocage membrane electrode assembling (MEA); Step 3: the ATP interacts with the cage polymer network molecules forming enhanced DER without a need for an external power supply.

Figure 5A:
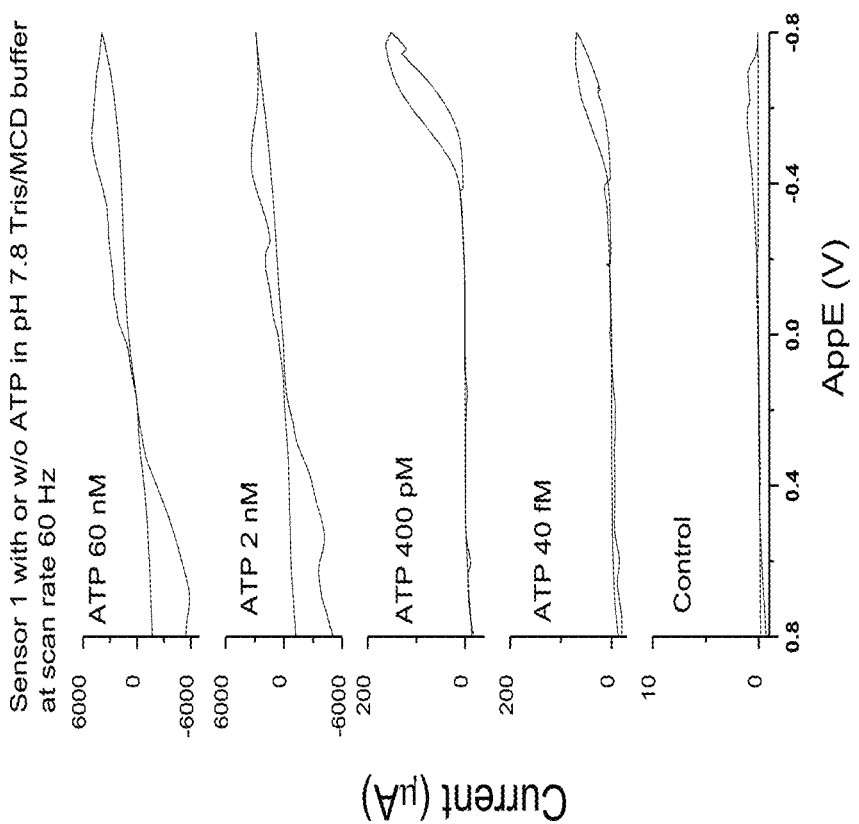
Figure 5B:
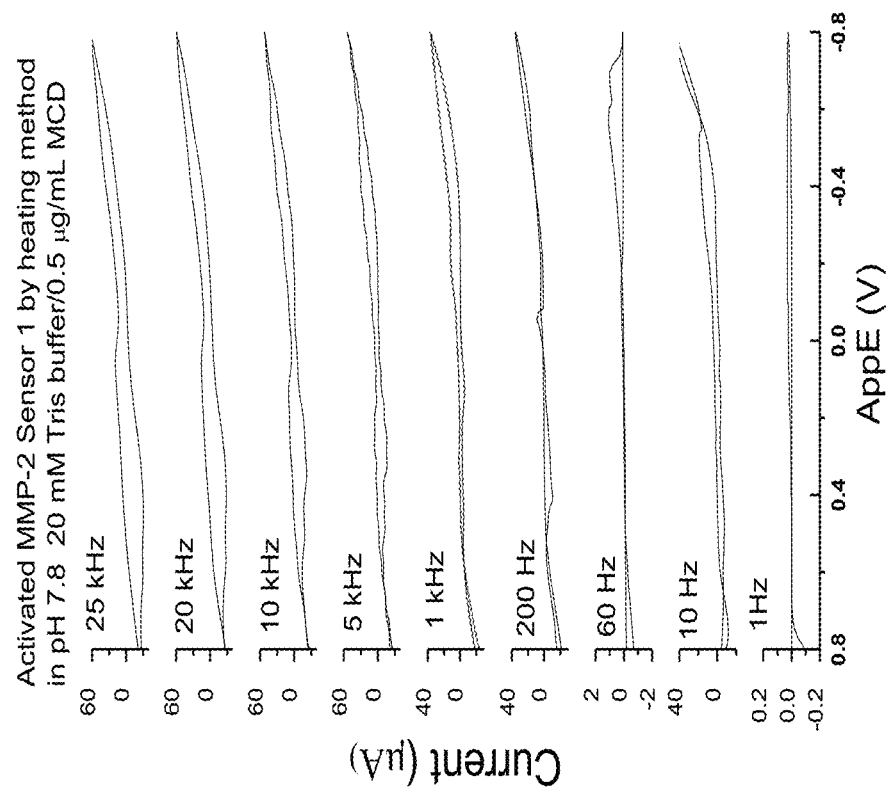

FIG. 5A depicts activated Sensor 1 by the heating method's i-V curves in different scan rates from 1 Hz to 25 kHz in pH 7.8 buffer (20 mM Tris/HCl buffer with 3 mM KCl, 130 mM NaCl and 0.5 mg/mL MCD), in short, as the Tris/HCl/MCD buffer. FIG. 5B depicts Sensor 1's i-V curves under the influence of ATP concentrations over 40 fM to 60 nM compared with the control under the scan rate of 60 Hz in the Tris media.

FIG. 6 depicts the scan rate impacts on the i-V curves of the activated state biomimetic MMP-2 Sensor 2, by the direct fabrication method, over scan rate from 1 Hz to 25 kHz in the tris/HCl/MCD media.

Figure 7:
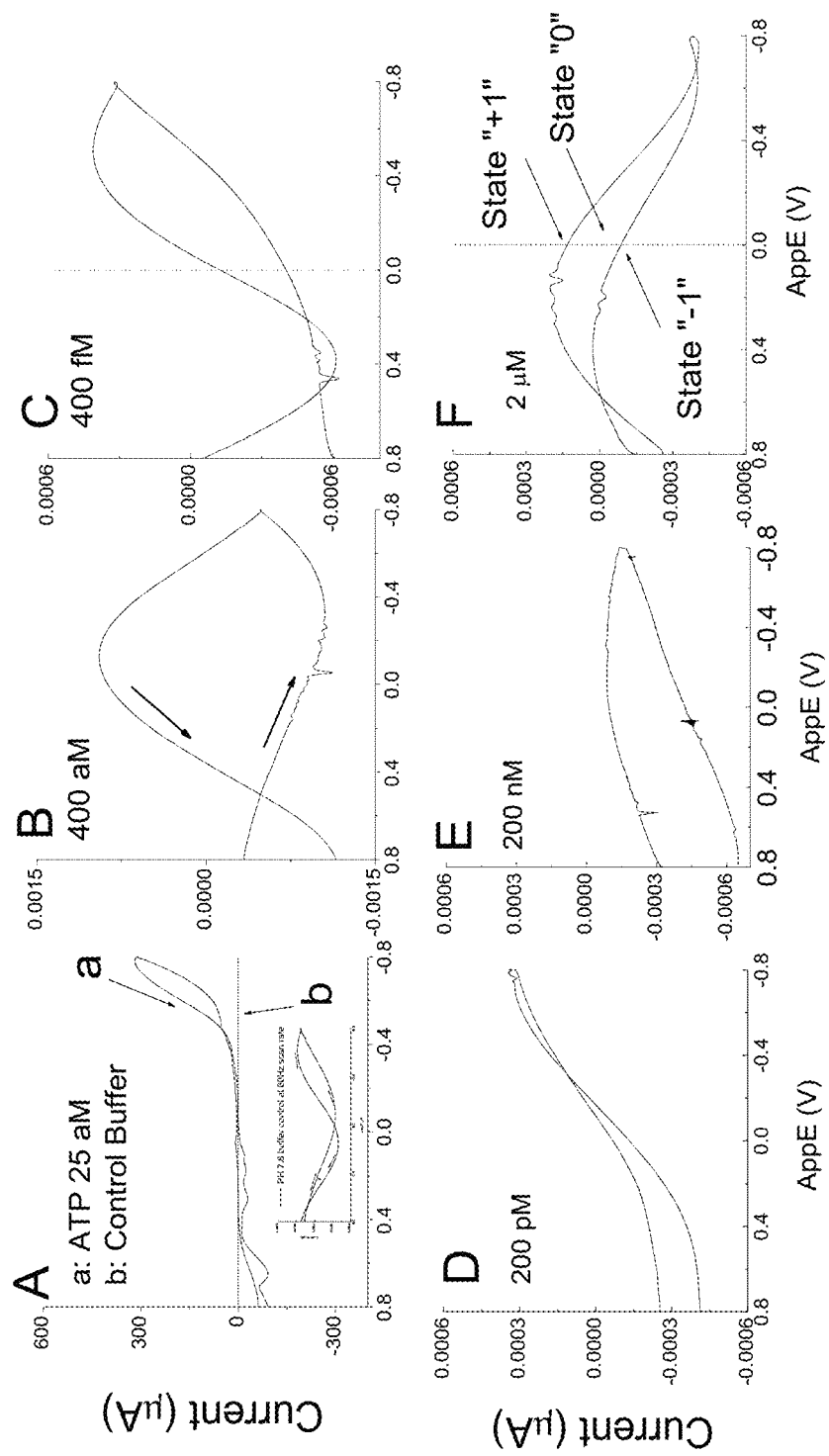

FIG. 7 depicts Sensor 2's i-V curves transformation between memristive to superconductive at zero-bias potential under the influence of ATP from 25 aM to 2 mM compared with the control with a 60 Hz scan rate in the tris/HCl/MCD media. Panel A is the i-V curve for ATP 25 aM compared with the control; Panel B is for the i-V curve having 400 aM; Panel C: is ATP 400 fM; Panel D: is ATP 200 pM; Panel E: ATP 200 nM; Panel F: ATP 2 mM.

FIG. 8 depicts the comparison of the superconducting i-V curves at the zero-bias potential for Sensor 2 under the influence of ATP from 200 fM to 200 mM compared with the control under a 10 kHz scan rate in the tris/HCl/MCD media. Panel A: is the control; Panel B: is ATP 200 fM; Panel C: is ATP 400 fM; Panel D: is ATP 200 pM; Panel E: is ATP 200 nM; Panel F: is ATP 400 nM; Panel G: ATP 800 nM; Panel H: ATP 2.0 mM, and Panel 1: ATP 200 mM in the media.

Figure 9:
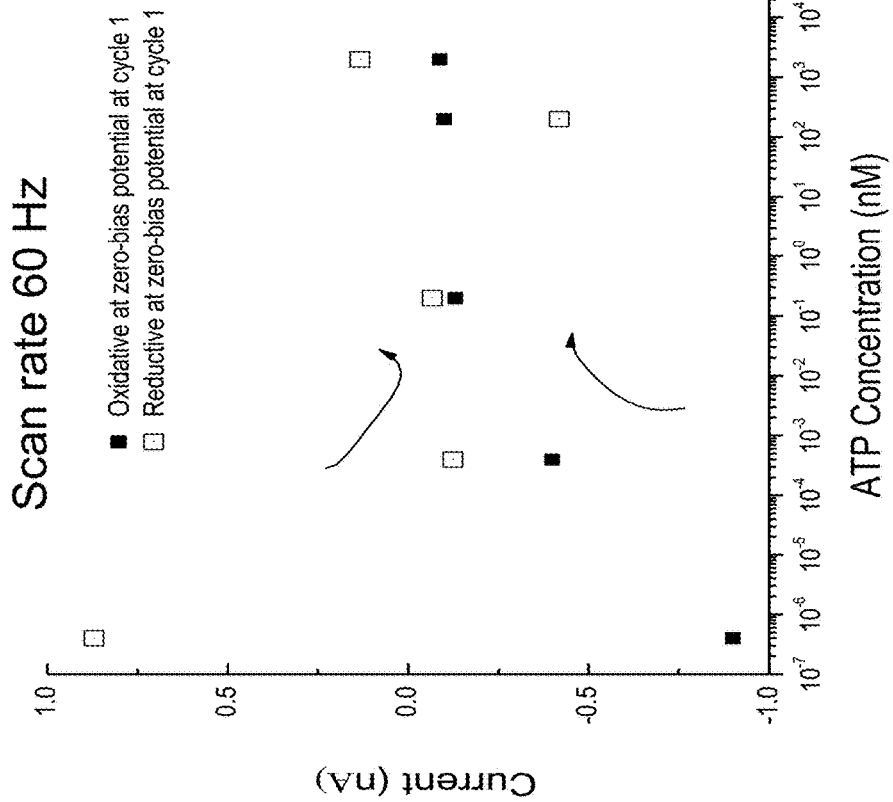

FIG. 9 depicts the supercurrent vs. ATP concentration curves of the $DET_{red}$ and $DET_{ox}$ peaks at the zero-bias potential with a 60 Hz scan rate for Sensor 2. The ATP concentration ranges from 400 aM to 2 mM. Data obtained according to Figures from FIG. 7B to 7F.

Figure 10:
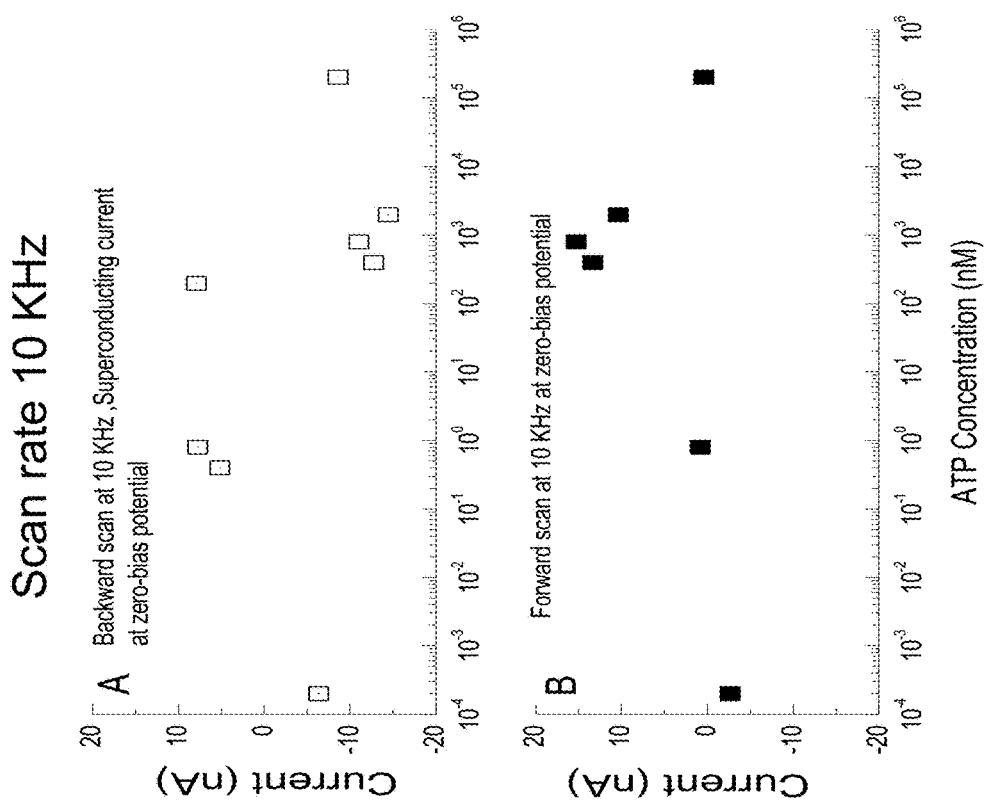

FIG. 10 depicts the supercurrent vs. ATP concentration curves of the $DET_{red}$ and $DET_{ox}$ peaks at the zero-bias potential at a 10 kHz scan rate for Sensor 2. The ATP concentration ranges from 200 fM to 200 mM. Data was obtained according to FIGS. 8A to 8I.

Figure 11:
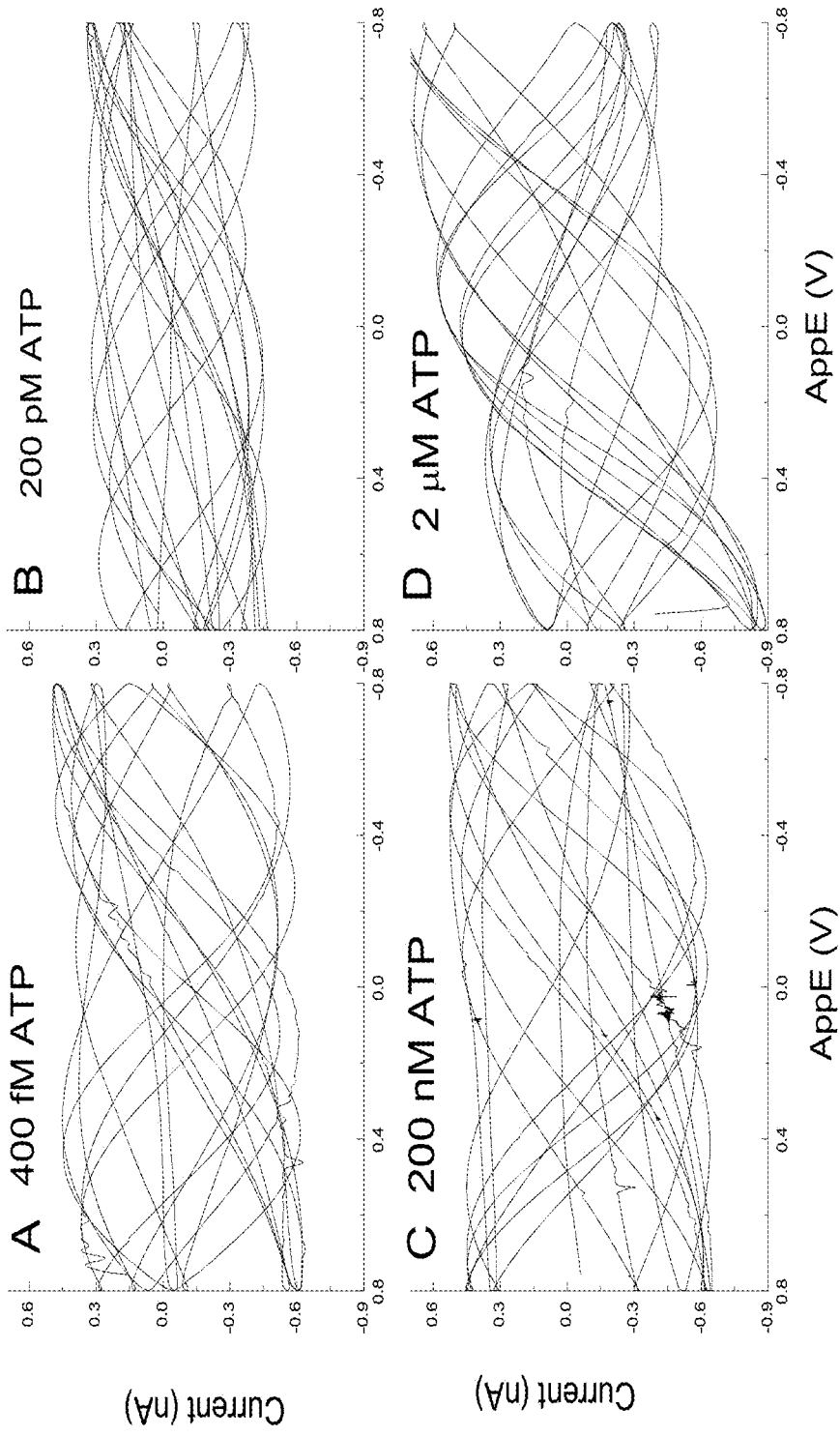

FIG. 11 depicts the impact of ATP concentrations at the Josephson junction on the supercurrent and the impact on the phase change of the waves at the zero-bias potential during 10 consecutive scans at 60 Hz over the ATP concentrations from 400 fM (Panel A), 200 pM (Panel B), 200 nM (Paneol C), and to 2.0 mM (Panel D) in the Tris/HCl/MCD media.

FIG. 12A depicts 25 aM low concentration ATP in consecutive 5 scan cycles of san rate 60 Hz i-V curves compared with the control of Sensor 2. There was no phase change occurring and keeping the hysteresis curves. FIG. 12B depicts 400 fM concentrations ATP in consecutive 9 scan cycles of san rate 60 Hz i-V curves compared with the control, having a phase change occur and superconducting at the zero-bias potential. FIG. 12C also depicts the presence of 200 nM ATP concentrations, Sensor 2 shows the phase change and superconducting current at a 60 Hz scan rate.

Figure 13:
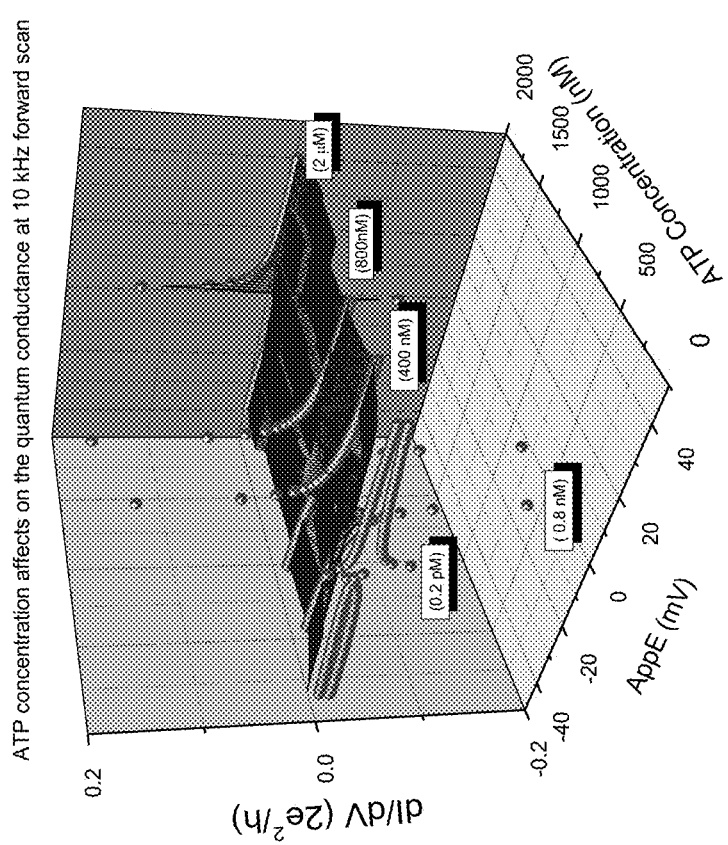

FIG. 13 depicts the 3D dynamic trap of the relationships over 5-level ATP concentrations from 0.2 pM to 2.0 mM over the potential range between −40 mV to +40 mV for illustration of the relationship among ATP concentrations, zero-bias potential, and the differential quantum conductance using 10 kHz scan rate forwarding scan data.

Figure 14:
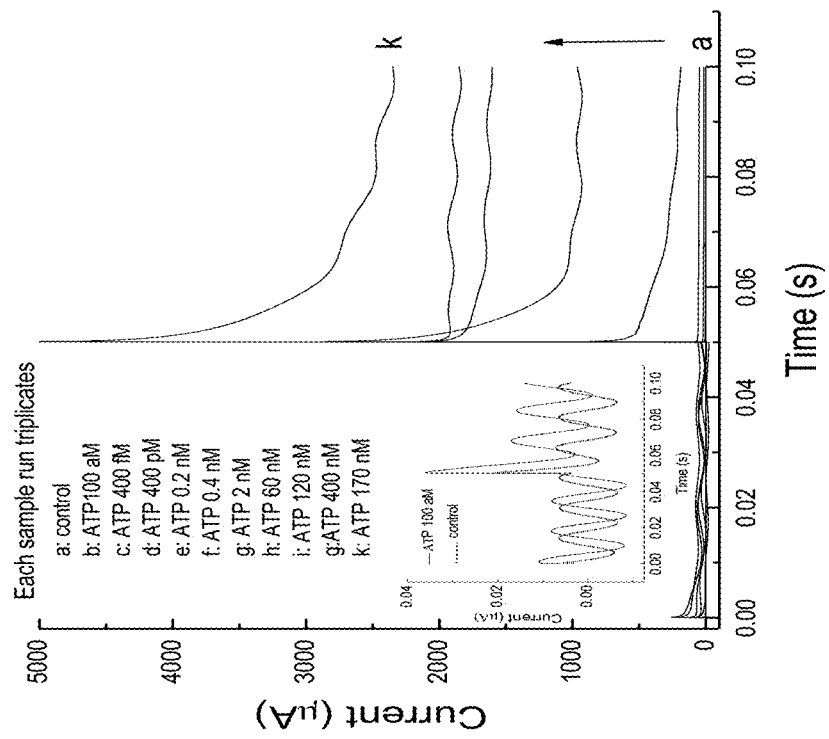

FIG. 14 depicts Sensor 1's real-time direct monitoring of current vs. time profiles over ATP concentrations over 100 aM to 400 nM (9 levels from curve a to k) vs. controls in the buffer solution. Samples run triplicates.

Figure 15:
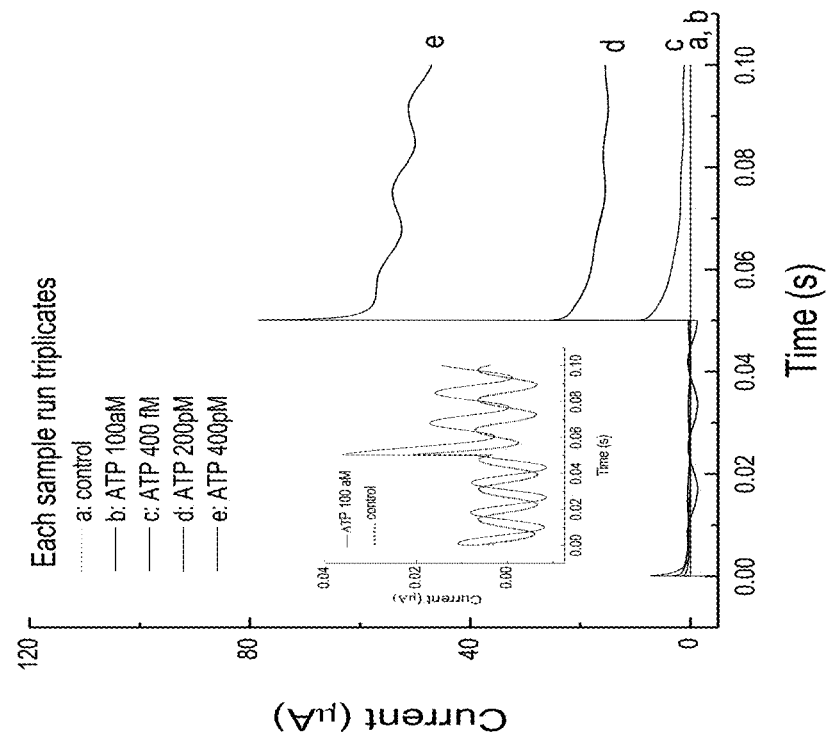

FIG. 15 depicts the lower-end concentration curves from a (the control) to e. Inserts are enlarged views for low-end concentration compared with controls.

Figure 16:
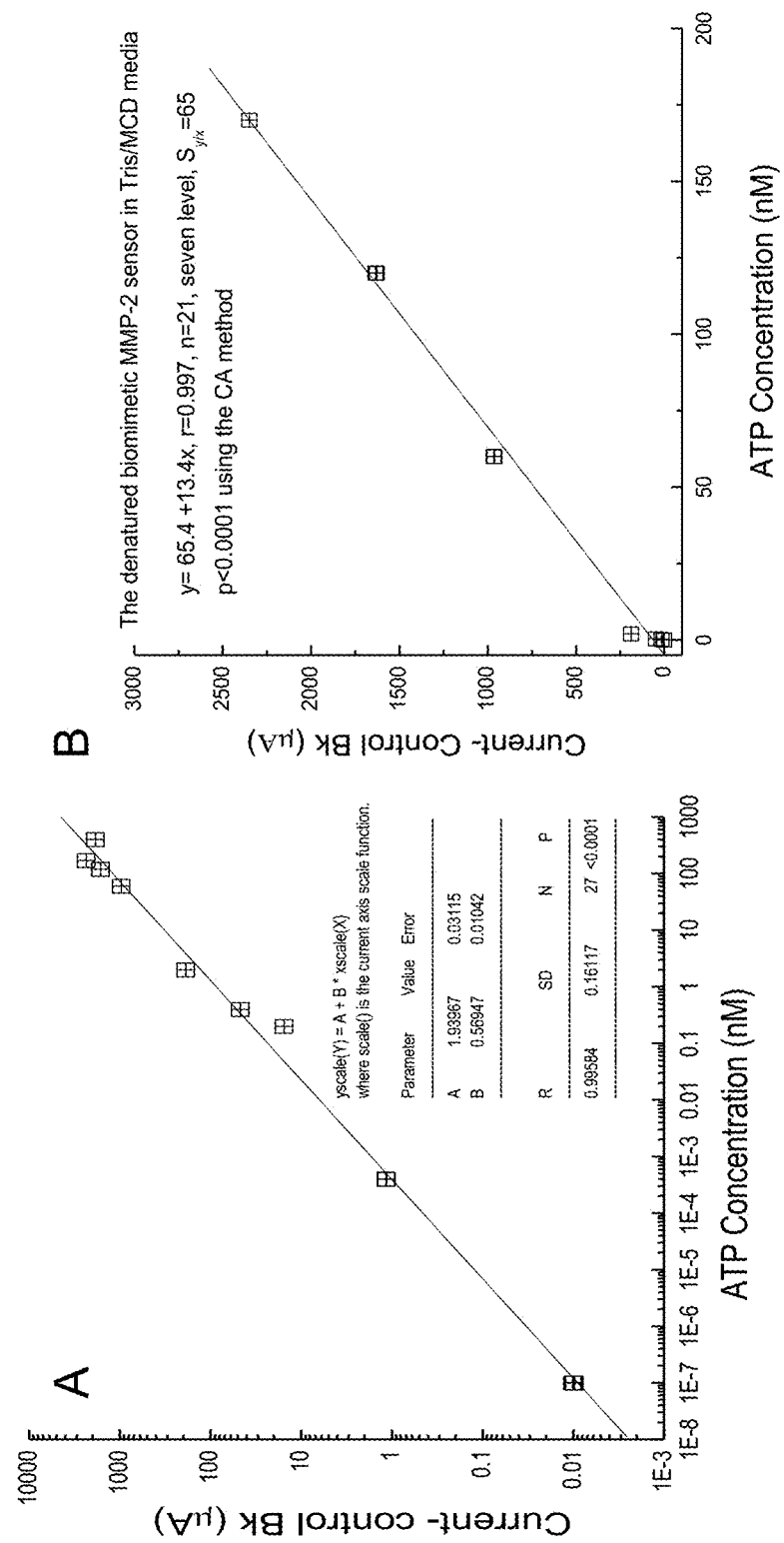

FIG. 16 Panel A depicts the calibration curve of current density after subtracting the background current vs. ATP over 100 aM to 170 nM. FIG. 16 Panel B depicts the calibration curve over the linear range from 400 fM to 170 nM. Each sample run triplicates.

Figure 17:
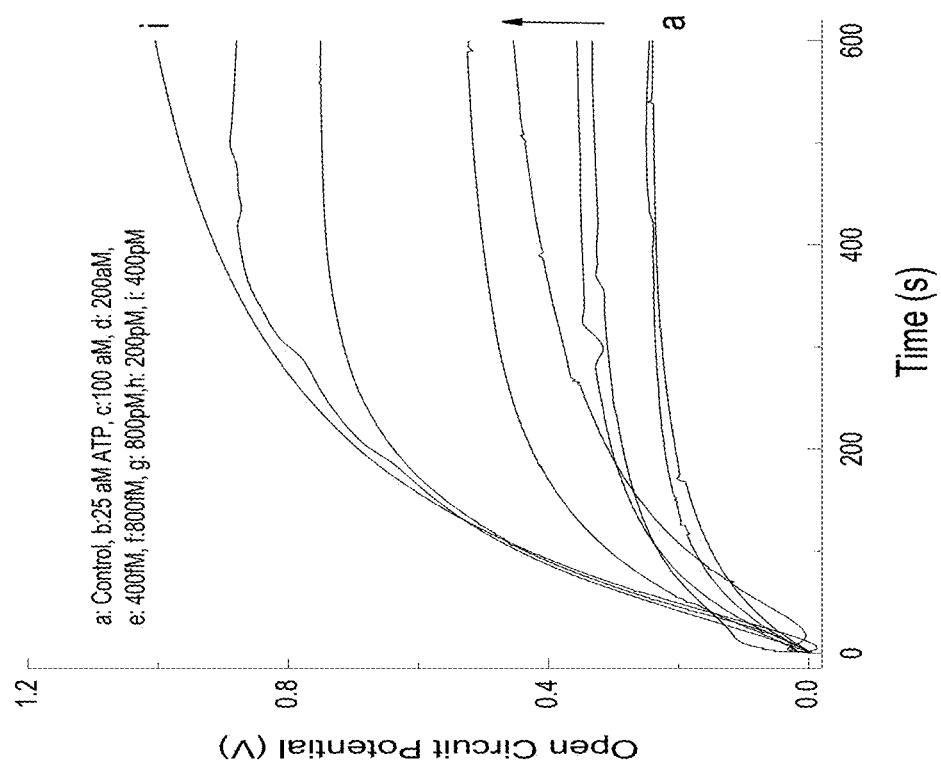

FIG. 17 depicts Sensor 2's open circuit potential curves for monitoring the energy change over 25 aM-400 pM ATP.

Figure 18:
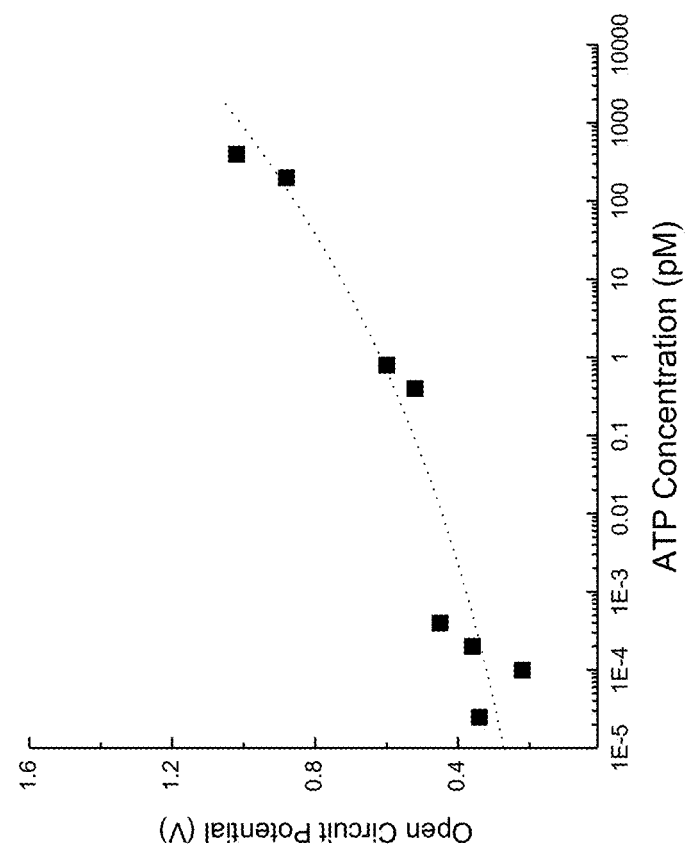

FIG. 18 depicts the calibration curve of voltage vs. ATP concentrations over 25 aM-400 pM.

Figure 19:
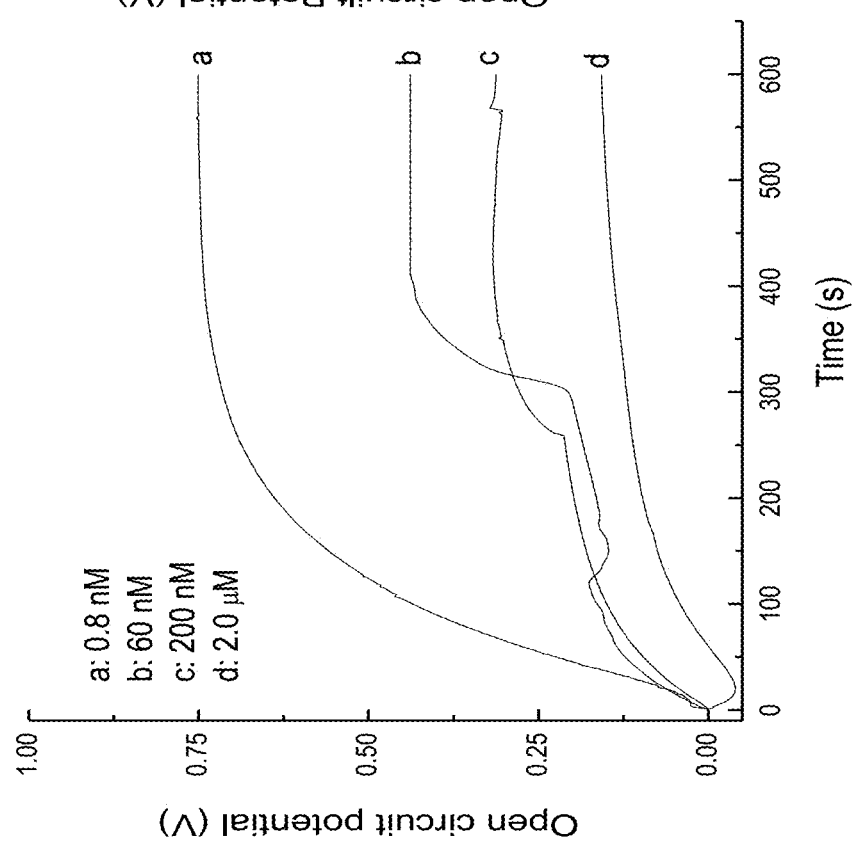

FIG. 19 depicts Sensor 2's open circuit potential curves at the high-end ATP concentration over 0.8 nM to 2.0 mM.

Figure 20:
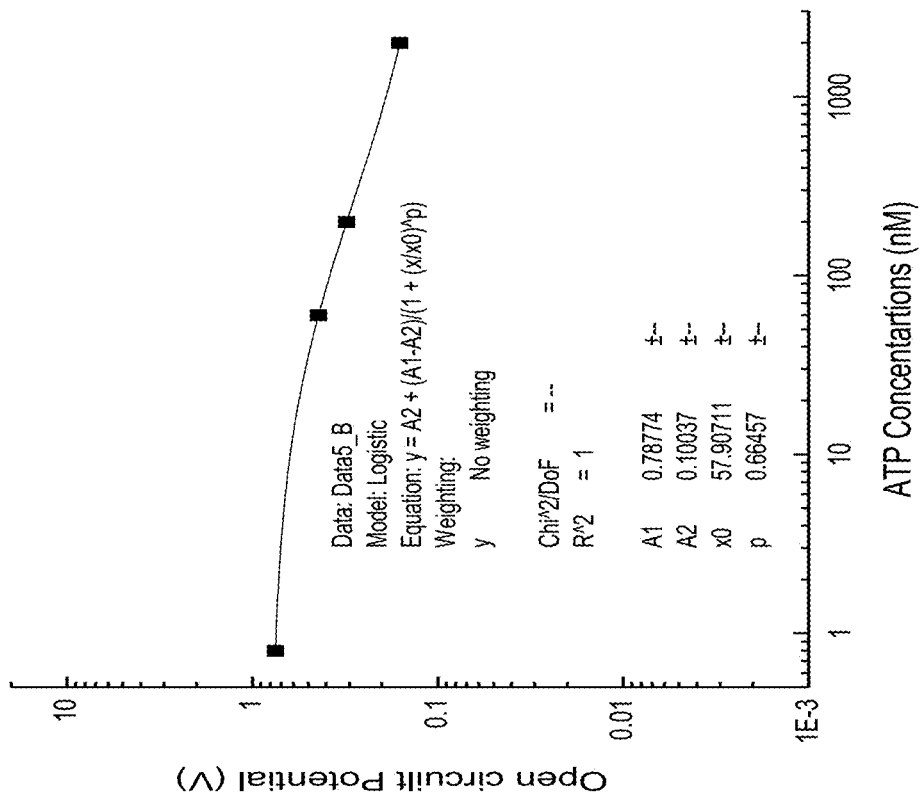

FIG. 20 depicts the double log plot of the calibration curve of the open circuit potential vs. ATP concentrations from 0.8 nM to 2.0 mM.

Figure 21:
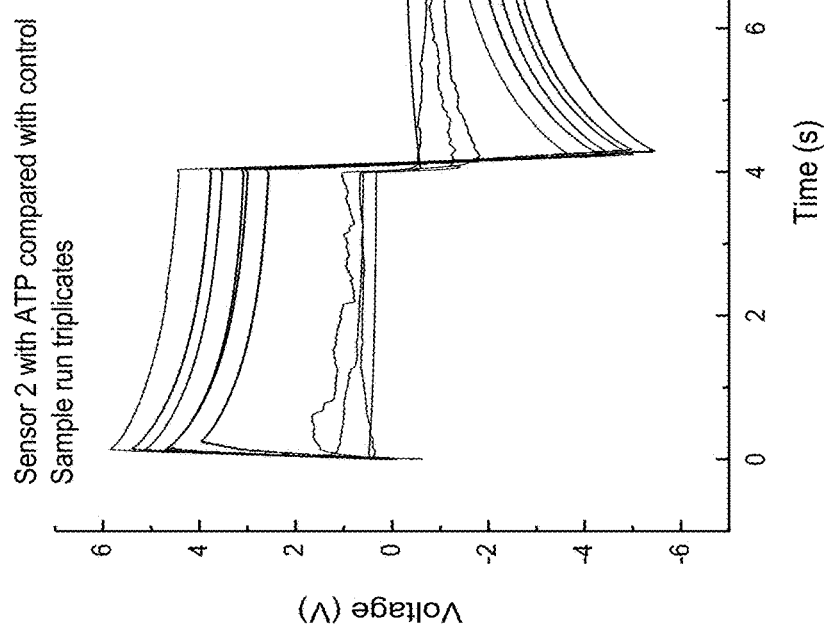

FIG. 21 depicts Sensor 2's voltage vs. time curves by the Double-step Chronopotentialmetry (DSCPO) method in the presence of various ATP concentrations from 25 aM to 400 nM in the Tris/HCl/MCD buffer compared with the control. Each sample run triplicates.

Figure 22A:
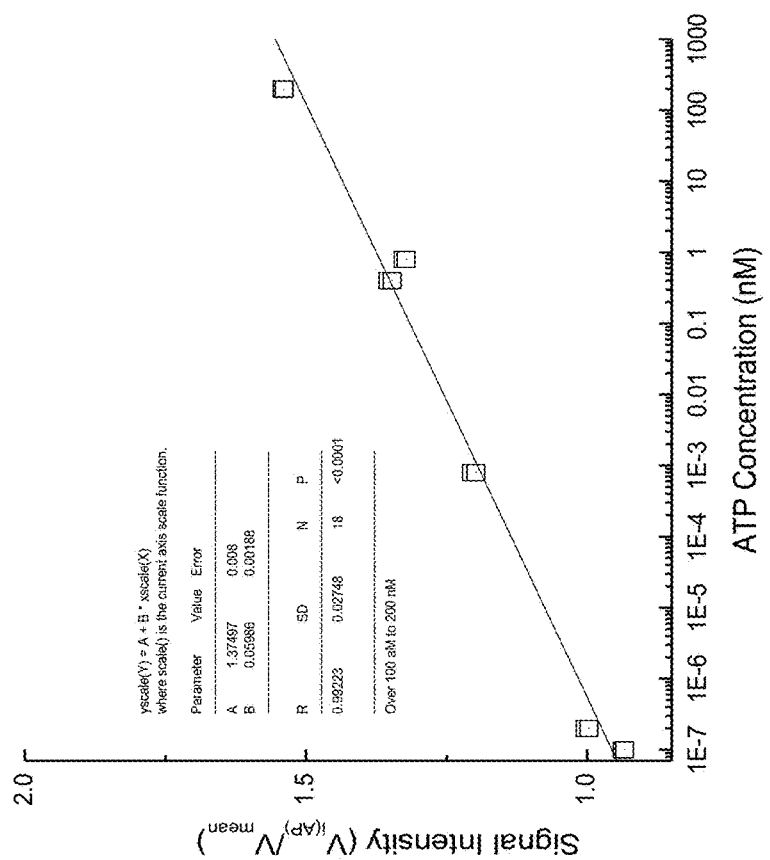
Figure 22B:
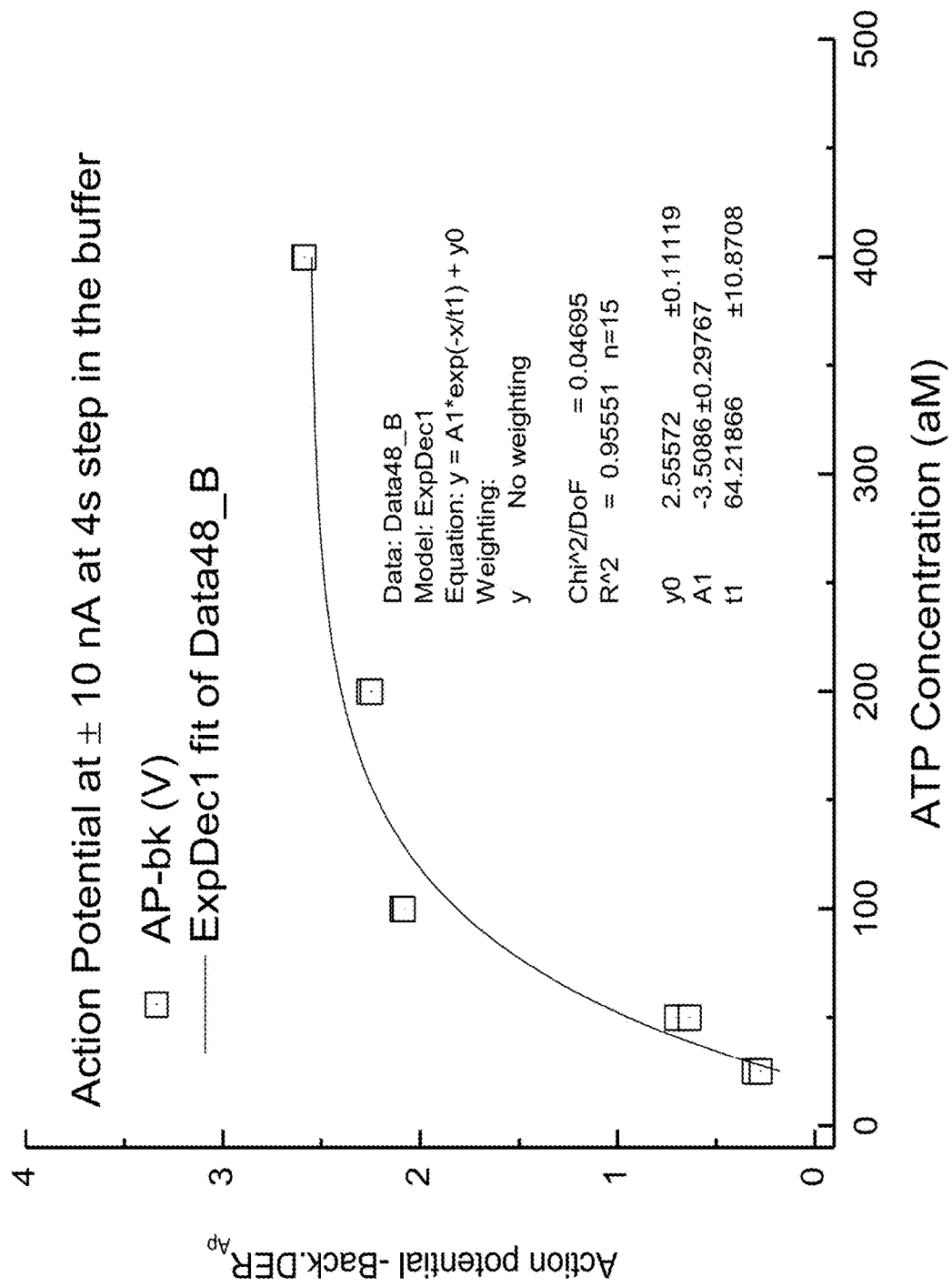

FIG. 22A depicts the calibration curve of the normalized action potential divided by the mean signal vs. ATP concentrations over 100 aM to 200 nM. FIG. 22B depicts the low-end ATP calibration curve from ATP 25 aM to 400 aM in the Action potential of the DER peak.

Figure 22C:
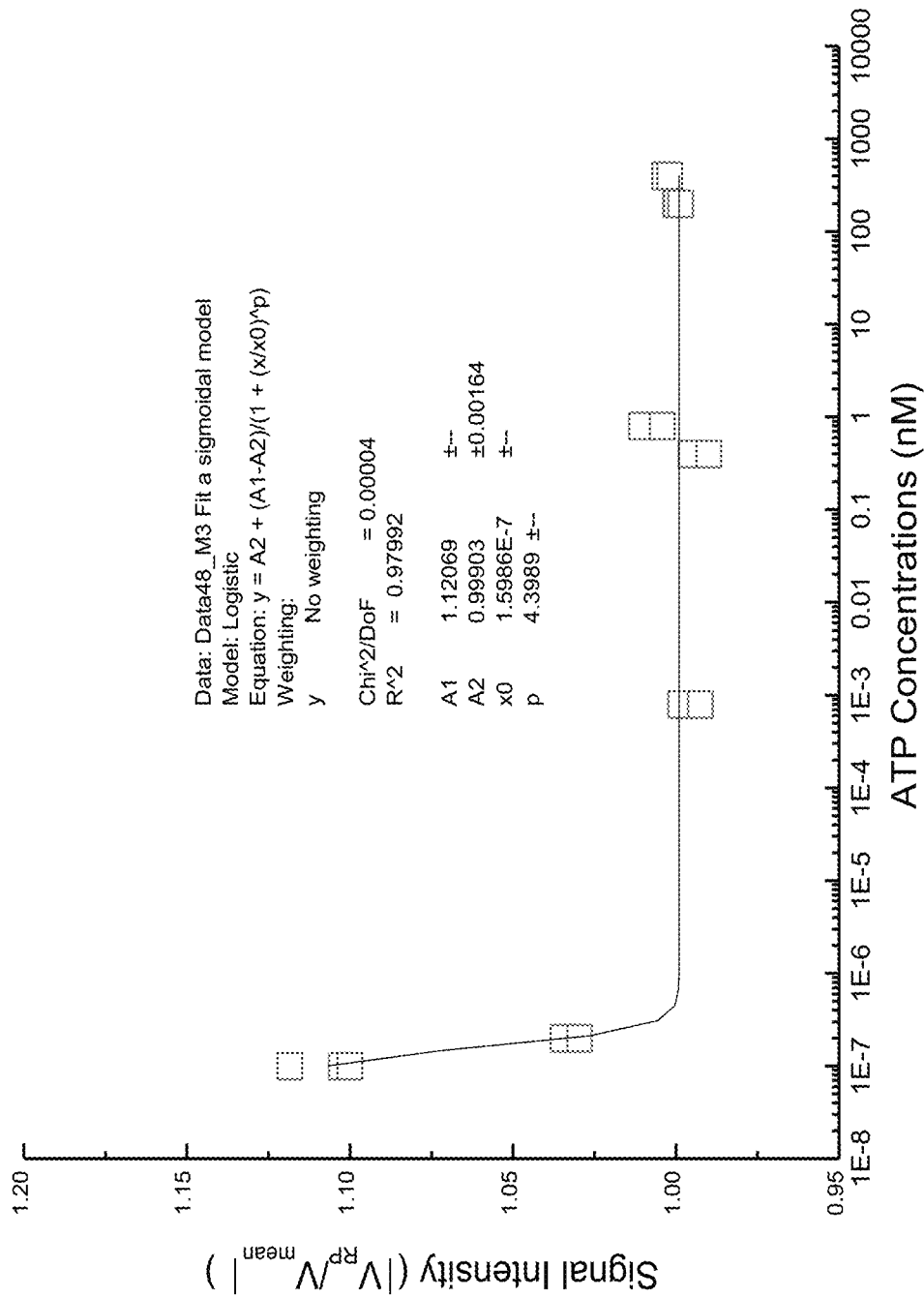

FIG. 22C depicts the semi-log plot of the absolute normalized resting potential vs. ATP concentrations under the same experimental conditions as FIG. 22A.

Figure 23:
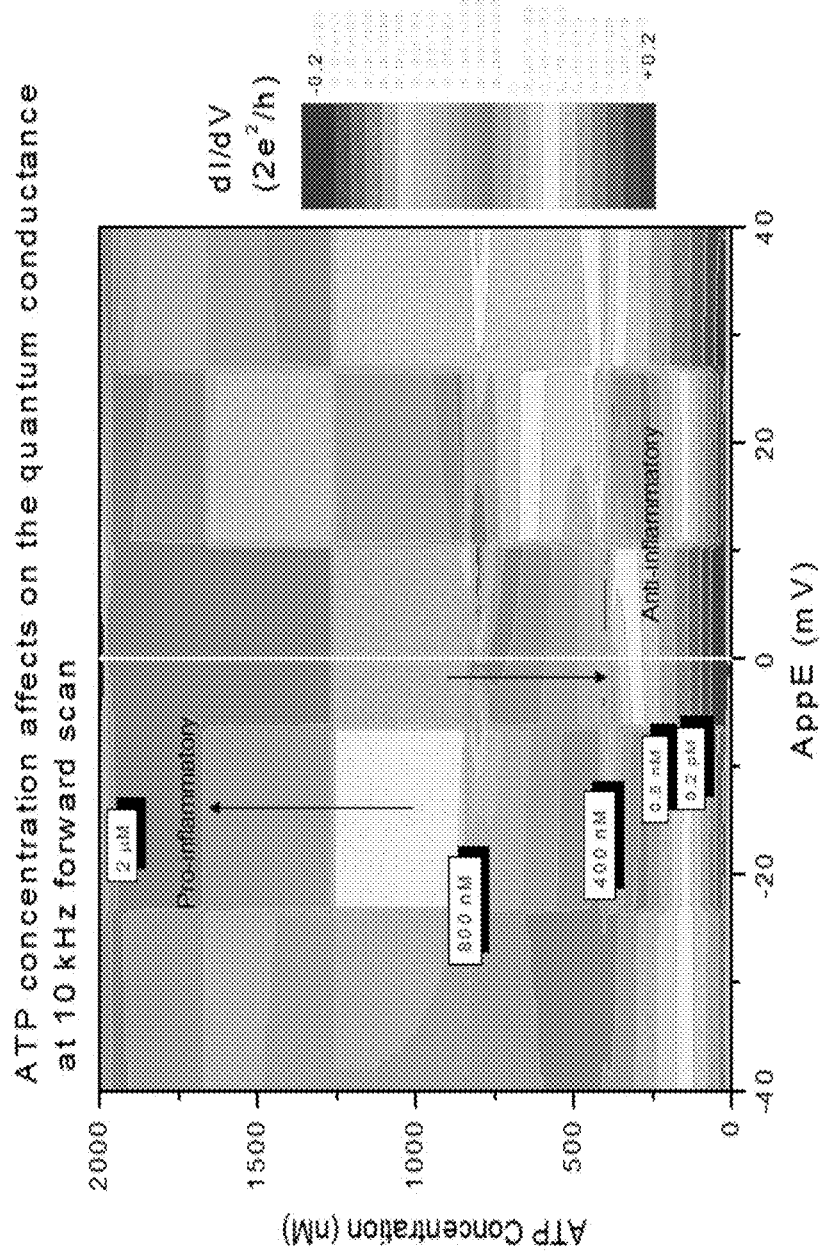

FIG. 22 D depicts a table that comprises Table 1 shows a comparison of method performance for quantitation of ATP spiked in the milk samples using the voltage method FIG. 23 depicts the Anti-inflammatory and the Pro-inflammatory counter map related to the ATP concentration at zero bias, and the quantum conductance for the "Healthy" HSP60 Sensor 2.

Figure 24:
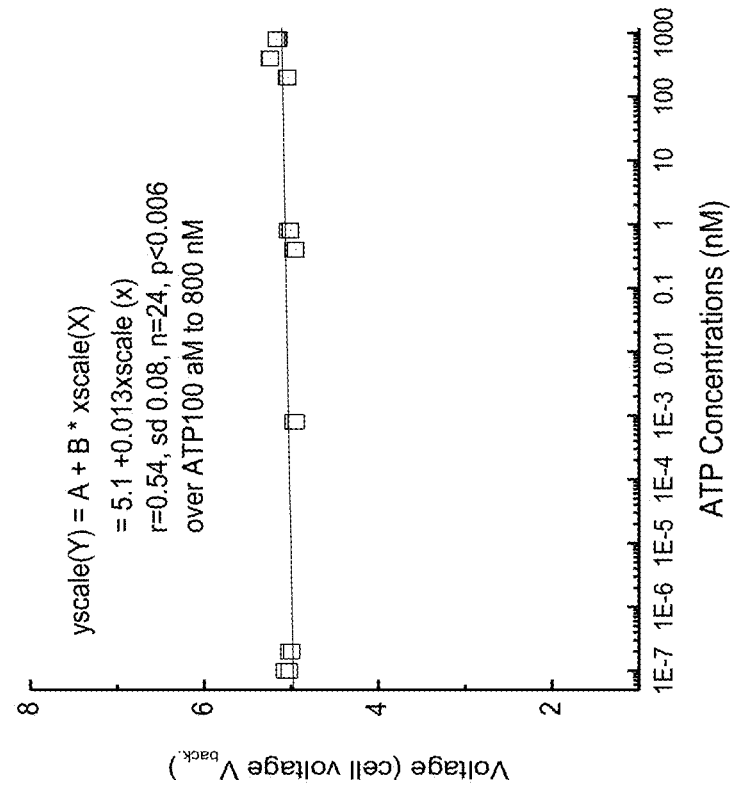

FIG. 24 shows the semi-log plot curve of the ATP concentration ranges effect on the cell Reversed Membrane Potential (RMP) (after subtracting the control). It was shown the trace is not depending upon the ATP concentrations between the range from 100 aM to 800 nM with n=24, eight concentration levels.

Figure 25:
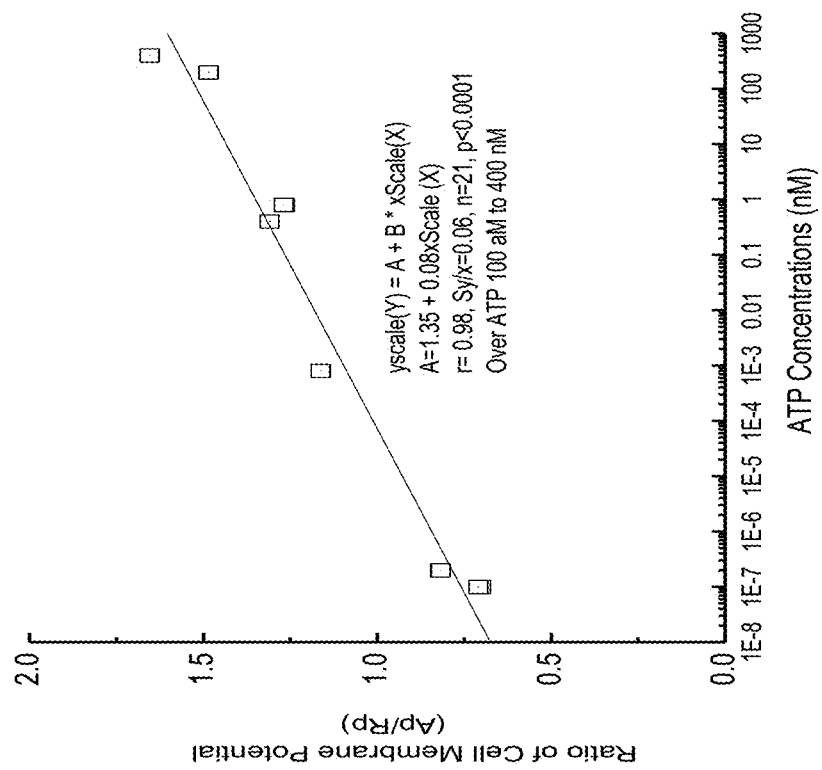

FIG. 25 depicts the semi-log plot curve of ATP concentration ranges effect on the ratio of action potential vs. resting membrane potential.

Figure 26:
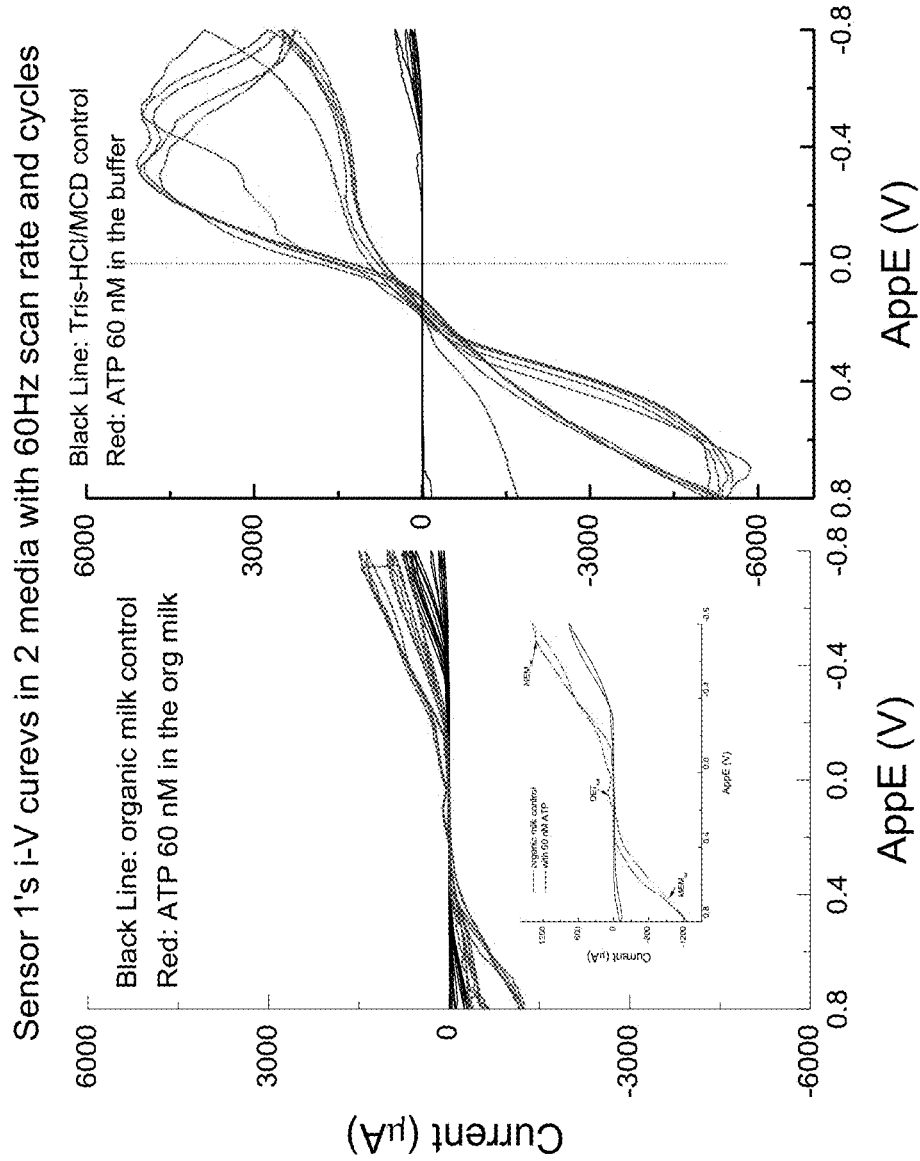

FIG. 26 Left Panel depicts the organic milk CV curves for current vs. applied potential in the presence of 60 nM ATP compared with the milk control (in black color) in 6 consecutive scans at 60 Hz. FIG. 26 Right Panel depicts the CV curves of 60 nM ATP (in red color) in buffer media and curves of the buffer control.

Figure 27:
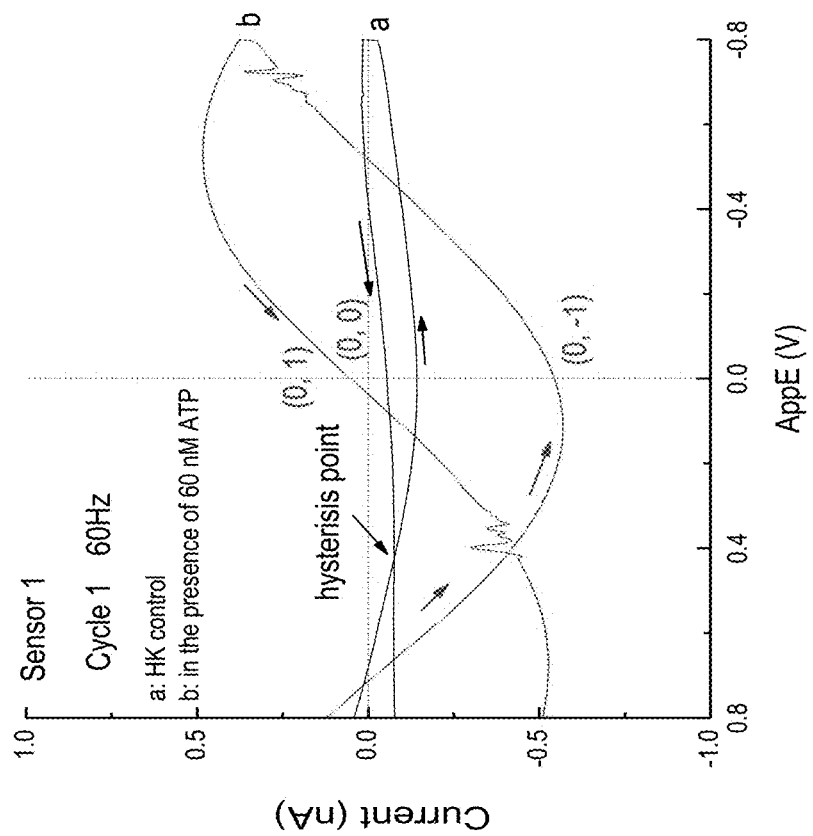

FIG. 27 depicts the DET peaks' current vs. scan cycles: the top Panel is for the DETred peak and the bottom Panel is for the DETox peak.

Figure 28A:
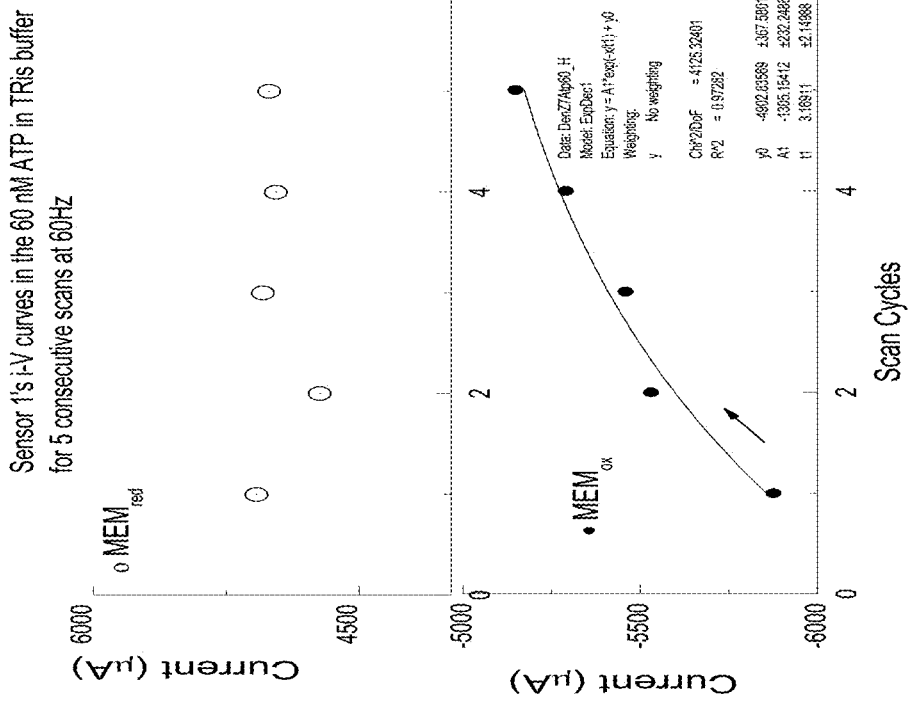
Figure 28B:
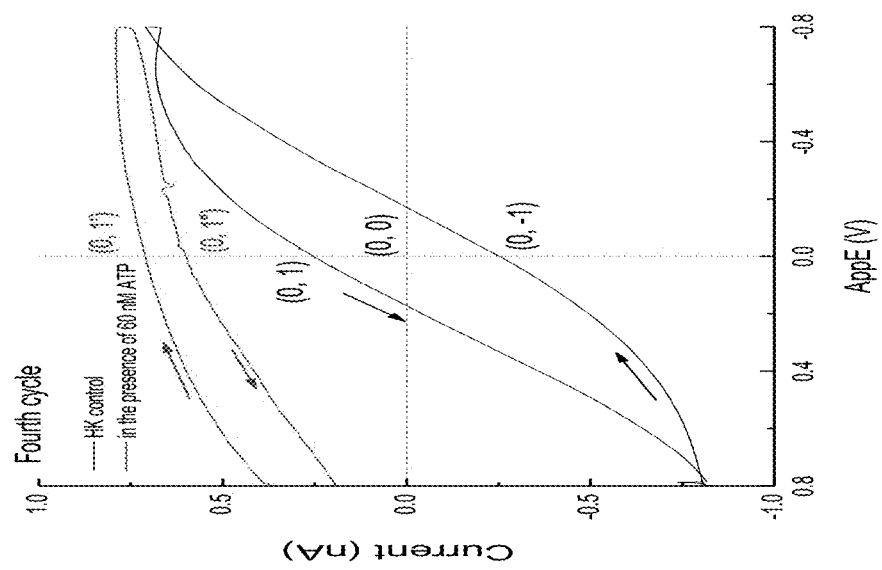
Figure 28C:
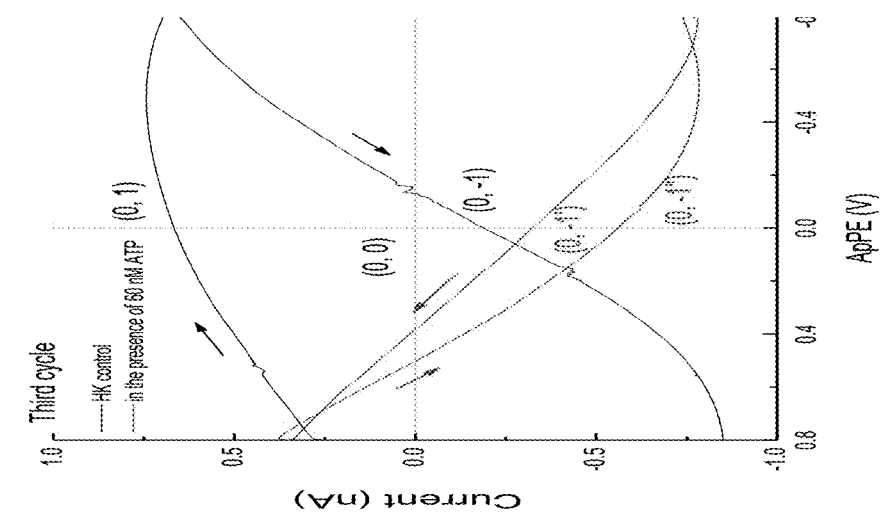
Figure 28D:
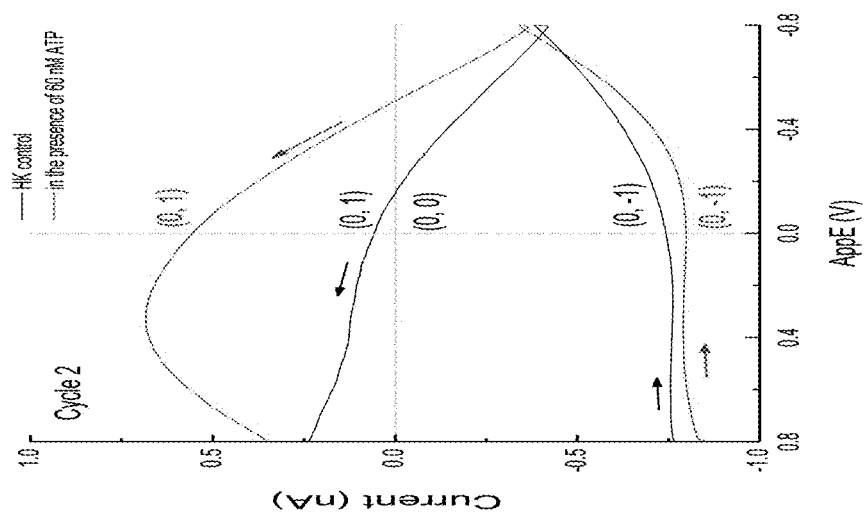

FIG. 28A depicts the first scan cycle at 60 Hz in the presence of 60 nM ATP (final concentration) in the human milk sample compared with the milk control sample. FIG. 28B depicts the second scan cycle at 60 Hz in the presence of 60 nM ATP (final concentration) in the human milk sample compared with the control milk sample. FIG. 28C depicts the third scan cycle. FIG. 28D depicts the fourth scan cycle.

Figure 29:
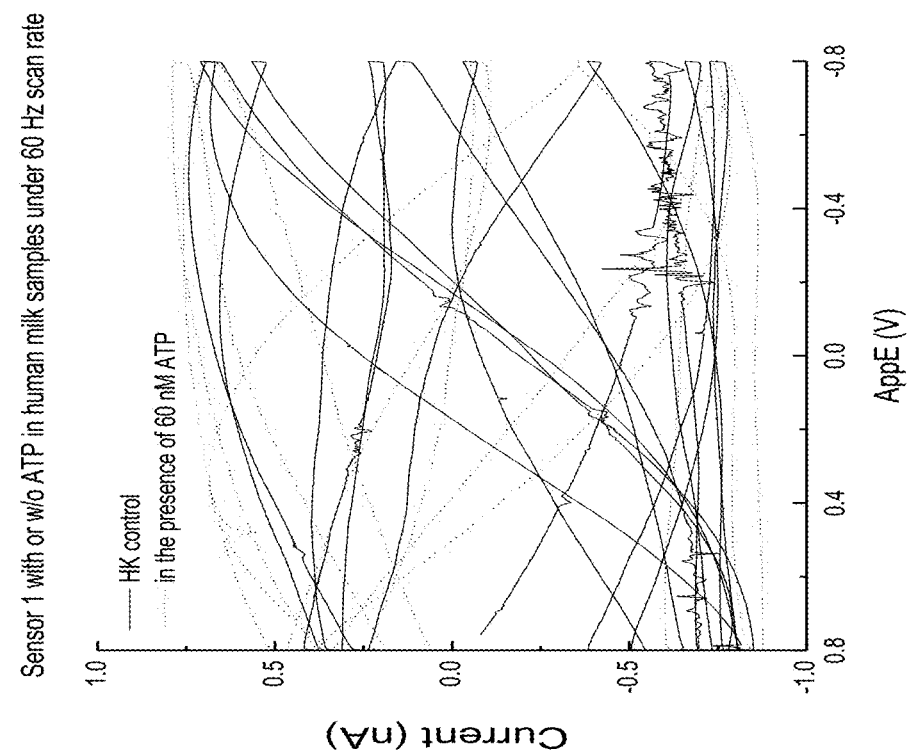

FIG. 29 depicts the alternative trends of the superconducting current at the zero-bias vs. scan cycles for the forward scan and backward scan compared with the human milk controls, respectively.

Figure 30:
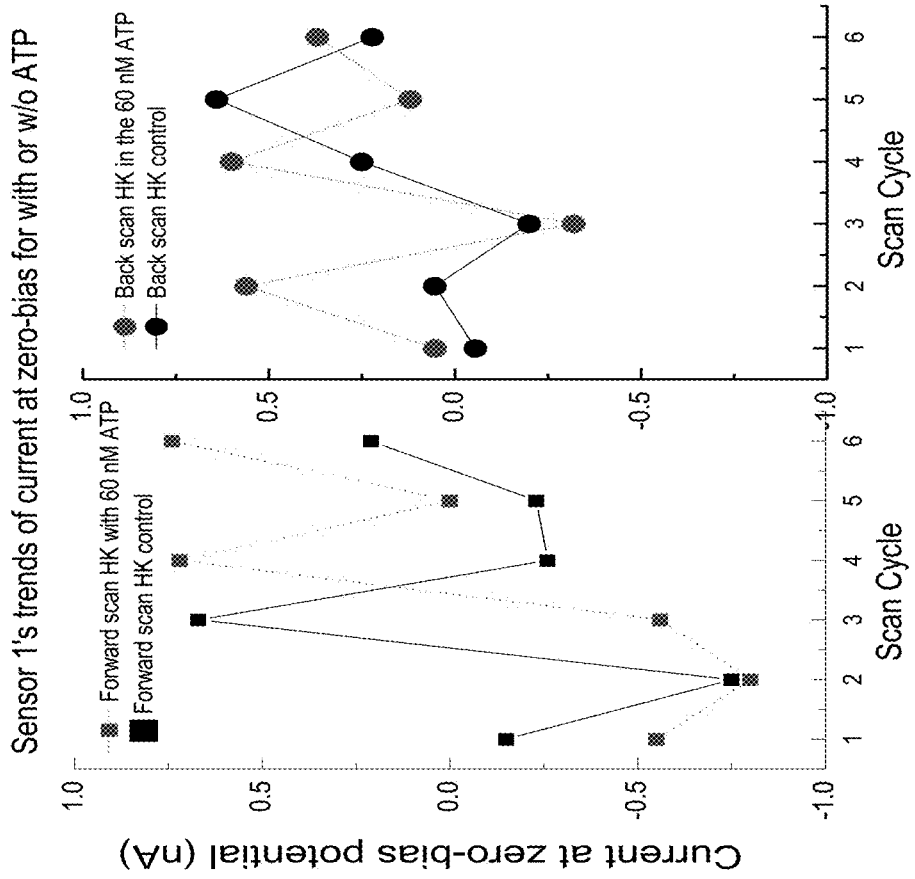

FIG. 30 depicts the overlapping curves of the control human milk sample in 6 consecutive scans vs. the milk sample with 60 nM ATP at 60 Hz.

EXAMPLE 1

Fabrication of the Membranes

Sensor 1 has an activated biomimetic MMP-2 membrane by a heating method at 80° C. for 5 minutes using the innate biomimetic MMP-2 membrane fabricated based on a published procedure [34]. Sensor 2 was also in a state of activation of biomimetic MMP-2 by a direct deposited method with compositions of TCD, PEG, PVP, bM-3-DMCD, and embedded zinc chloride on gold chips with appropriate proportions at 370 C for 96 hours. The morphology of the AU/SAM was characterized using an Atomic Force Microscope (AFM) (model Dimension Edge AFM, Bruker, MA).

EXAMPLE 2

The Friedel-Oscillation in the Superlattice Membranes

Figure 1A:
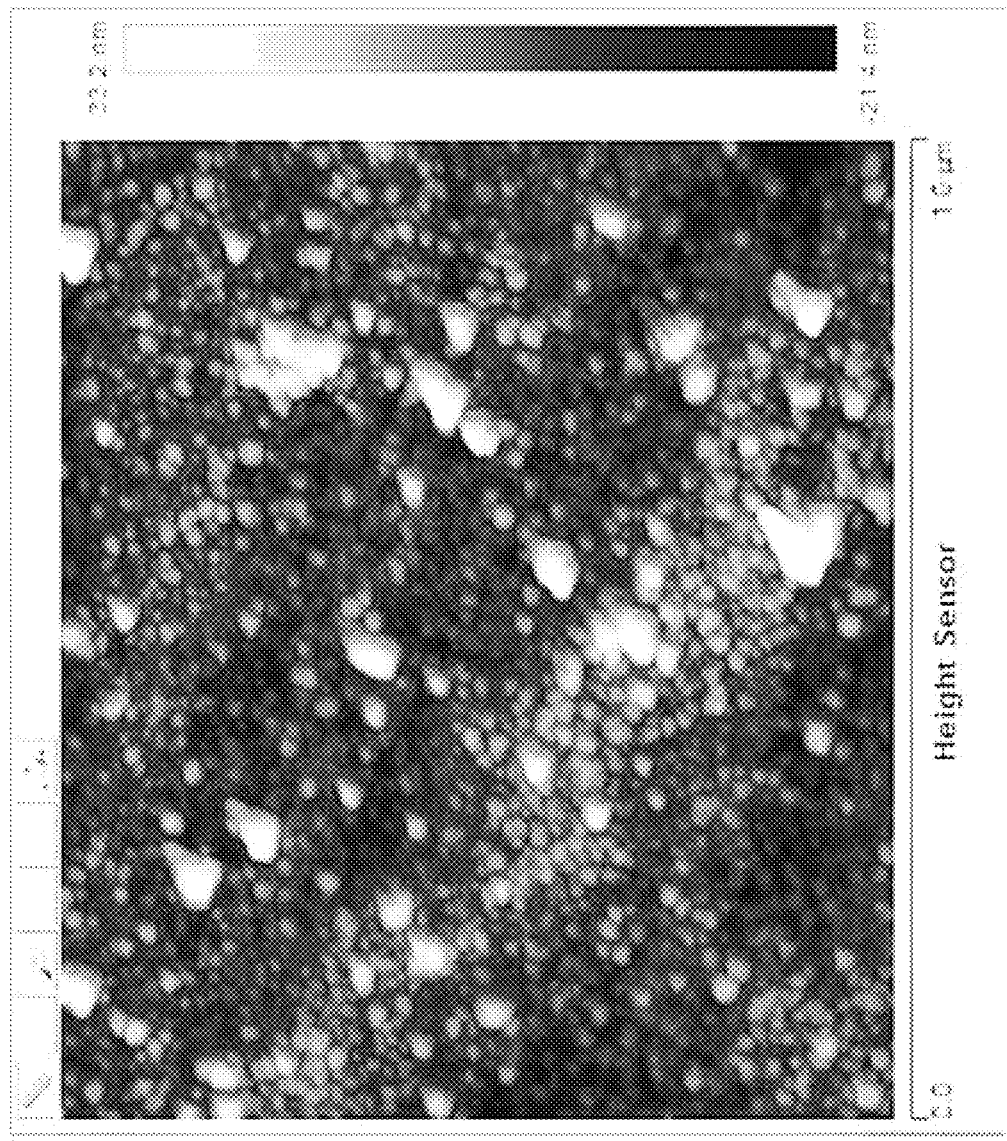
FIG. 1A depicts the 2D AFM membrane image in the native state of the biomimetic MMP-2 device.

Friedel oscillation is a phenomenon of long-range indirect interactions between electrons on a superlattice surface [21]. Evaluations of the Friedel-oscillation were conducted based on the AFM images. FIG. 1A revealed the strong Friedel-oscillation with a flame-like electric cloud surrounding the zinc atoms which the "cloud" moves toward the same direction in the 1.0 μm² area. This is the evidence of the Cooper pair transmission waves at the Josephson junction. The image was for the biomimetic "native" MMP-2 membrane, i.e., the membrane comprised of triacetyl-β-cyclodextrin (TCD), polyethylene glycol diglycidyl ether (PEG), poly(4-vinyl pyridine) (PVP), bis-substituted imidazole dimethyl-β-cyclodextrin (bM-β-DMCD), cysteine and embedded zinc chloride in appropriate proportions. The native MMP-2 protein has two states: an innate state with the cysteine "on" and an activated state with the cysteine "off".

Figure 1B:
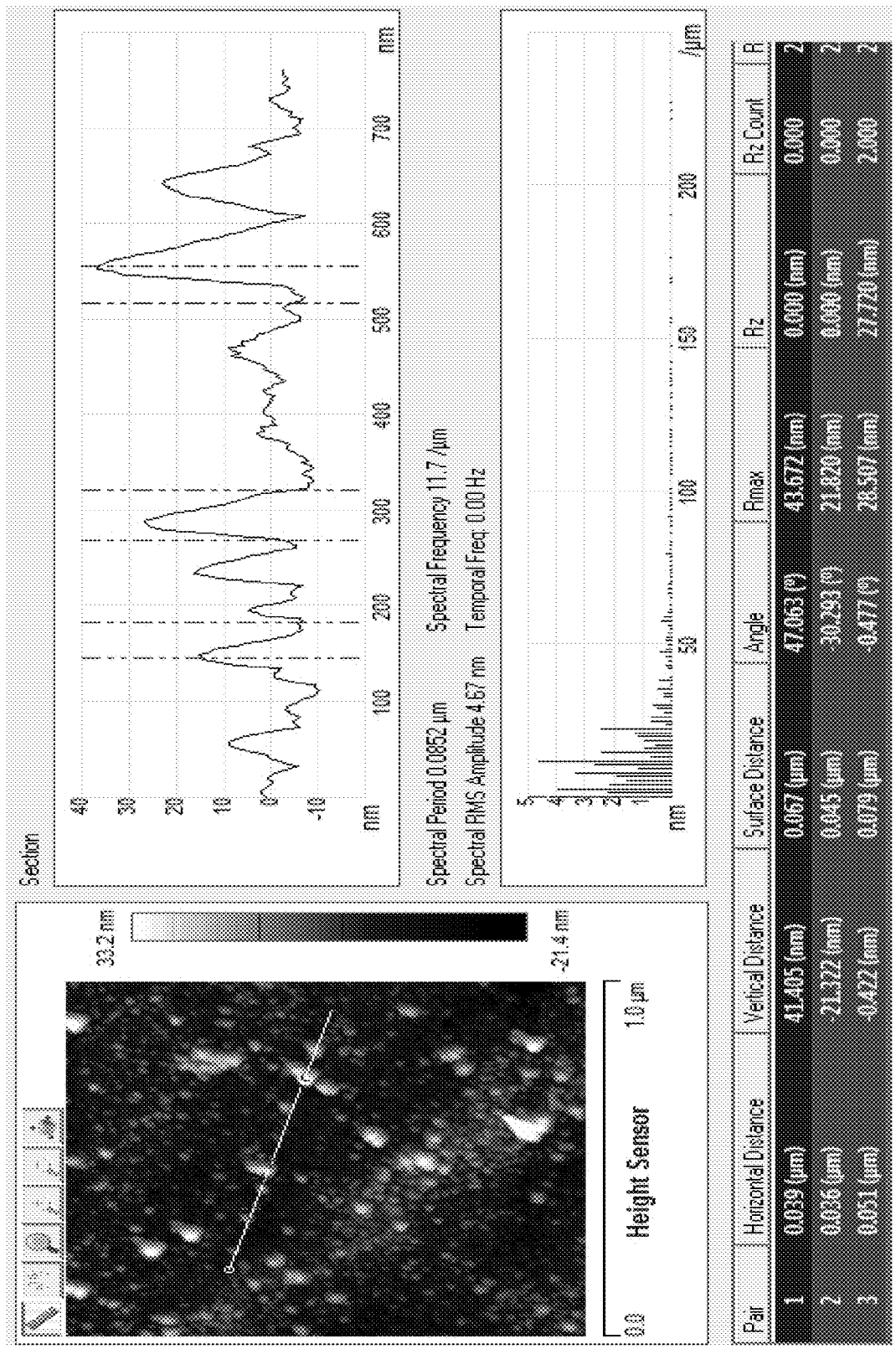
FIG. 1B depicts the cross-section analysis of the AFM membrane image.
Figure 2A:
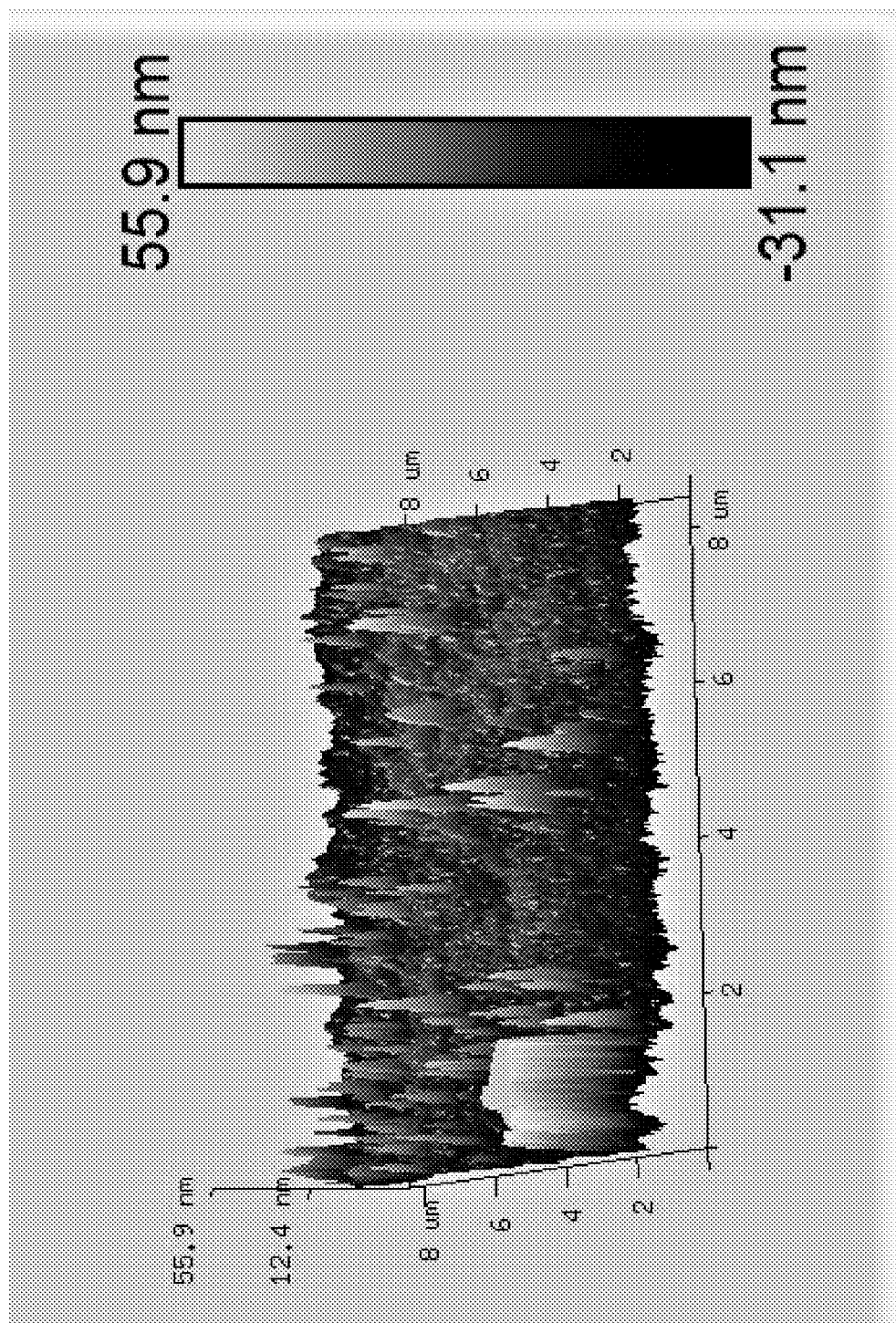
FIG. 2A depicts the 3D AFM image of the activated biomimetic MMP-2 Sensor 1 by the heating method.
Figure 2B:
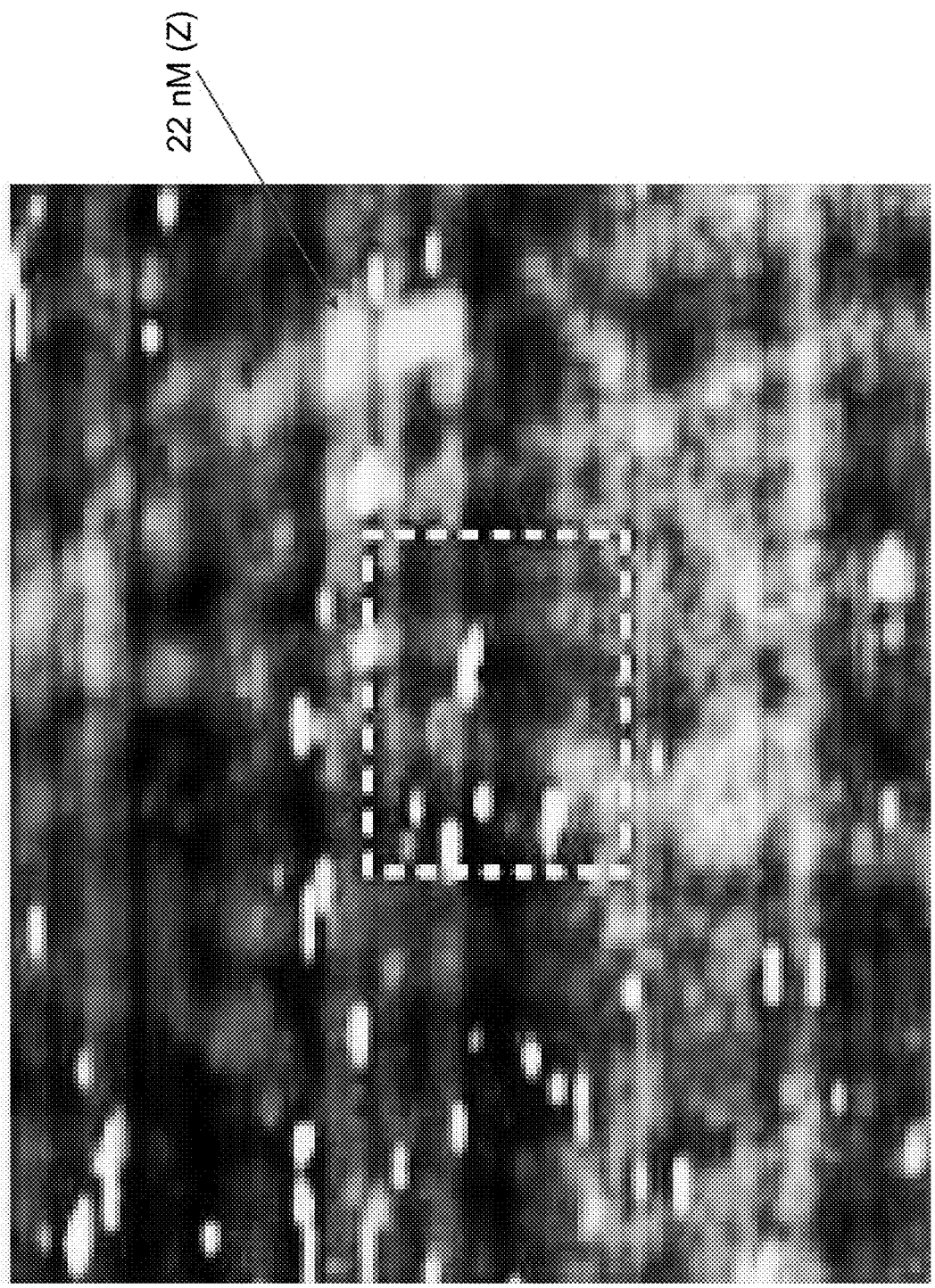
FIG. 2B depicts the enlarged 2D AFM image with the same z-value range between 33.2 to −21.4 nm as the native state device in FIG. 1A for comparison.

FIG. 1A depicts the 2D AFM membrane image in the native state of the biomimetic MP-2 device. FIG. 1B depicts the cross-section analysis of the AFM membrane image. FIG. 1A was with the cysteine "On" in its innate state, and we observed the Cooper pair electrons moving toward the same direction. FIG. 2A depicts the 3D AFM image of the activated biomimetic MMIP-2 Sensor 1 by the heating method. FIG. 2B depicts the enlarged 2D AFM image with the same z-value range between 33.2 to −21.4 nm as the native state device in FIG. 1A for comparison. Sensor 1 has an activated biomimetic MMP-2 membrane by a heating method to kick out the cysteine group in the network, as evidence, we did not observe moving Cooper pairs in FIG. 2A, the labeled square has the same Z range as shown in FIG. 1A. The matrix of the superlattice was shown partially damaged shown in FIG. 2B.

Figure 3A:
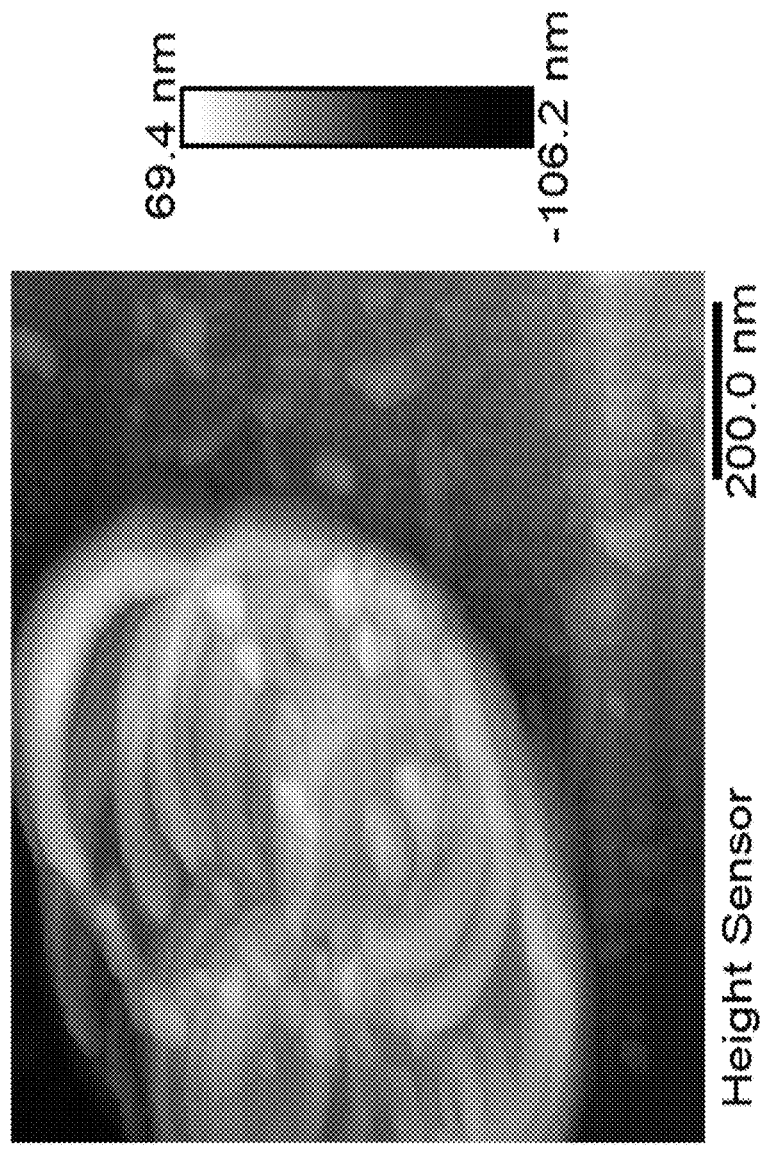
FIG. 3A depicts the 2D image of the multiple-layer ring structure of the activated biomimetic MMP-2 Sensor 2 by the direct fabrication method in 0.734×0.734 µm². The ring structure parameters labeled as "1" are listed.

FIG. 3A depicts the 2D image of the multiple-layer ring structure of the activated biomimetic MMP-2 Sensor 2 by the direct fabrication method in 0.734×0.734 µm². The ring structure parameters labeled as "1" are listed. The inner ring diameter is about 161 nm, and the out ring diameter is 192 nm. Sensor 2 was directly fabricated using the same polymers and other compositions such as bM-β-DMCD/TCD/PEG/PVP/ZnCl², except without cysteine. The Friedel-oscillation was observed in two locations in FIG. 3A.

Figure 3B:
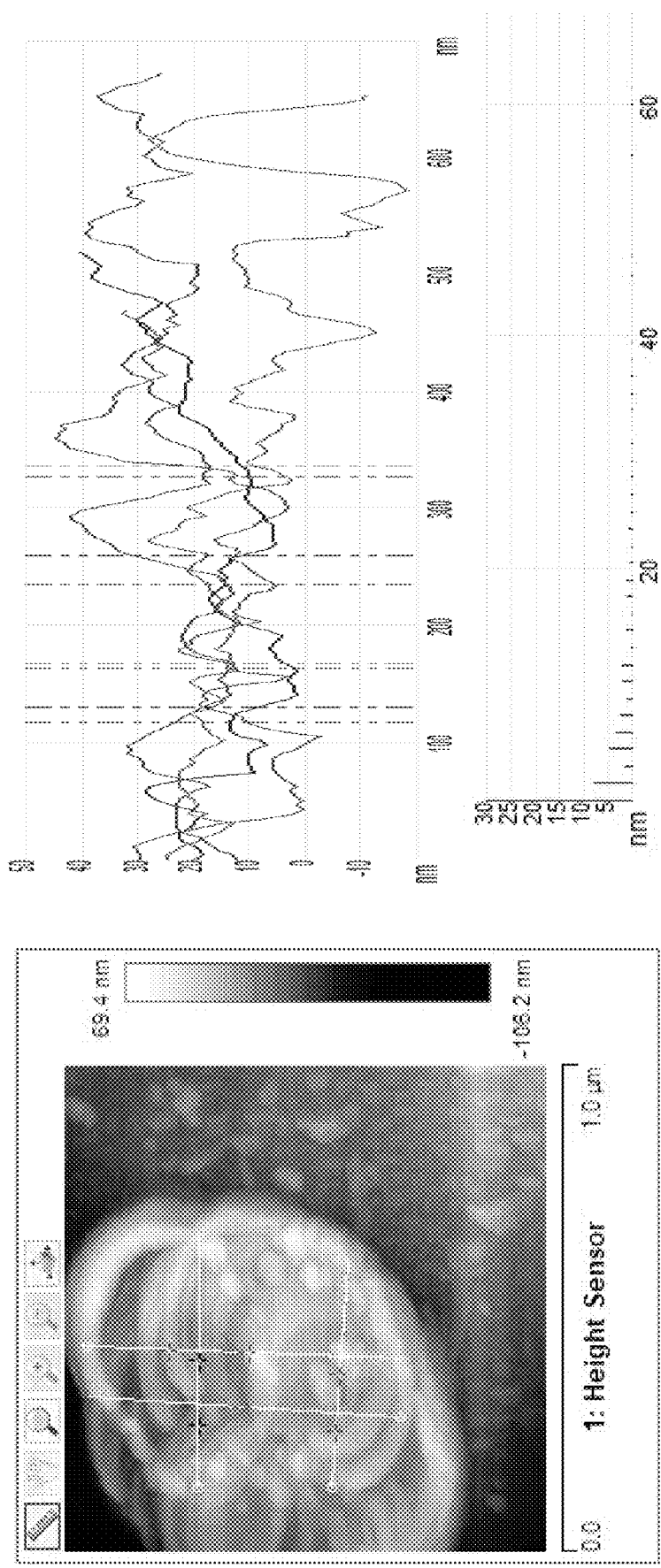
FIG. 3B depicts the cross-section analysis of the AFM membrane image.
Figure 3C:
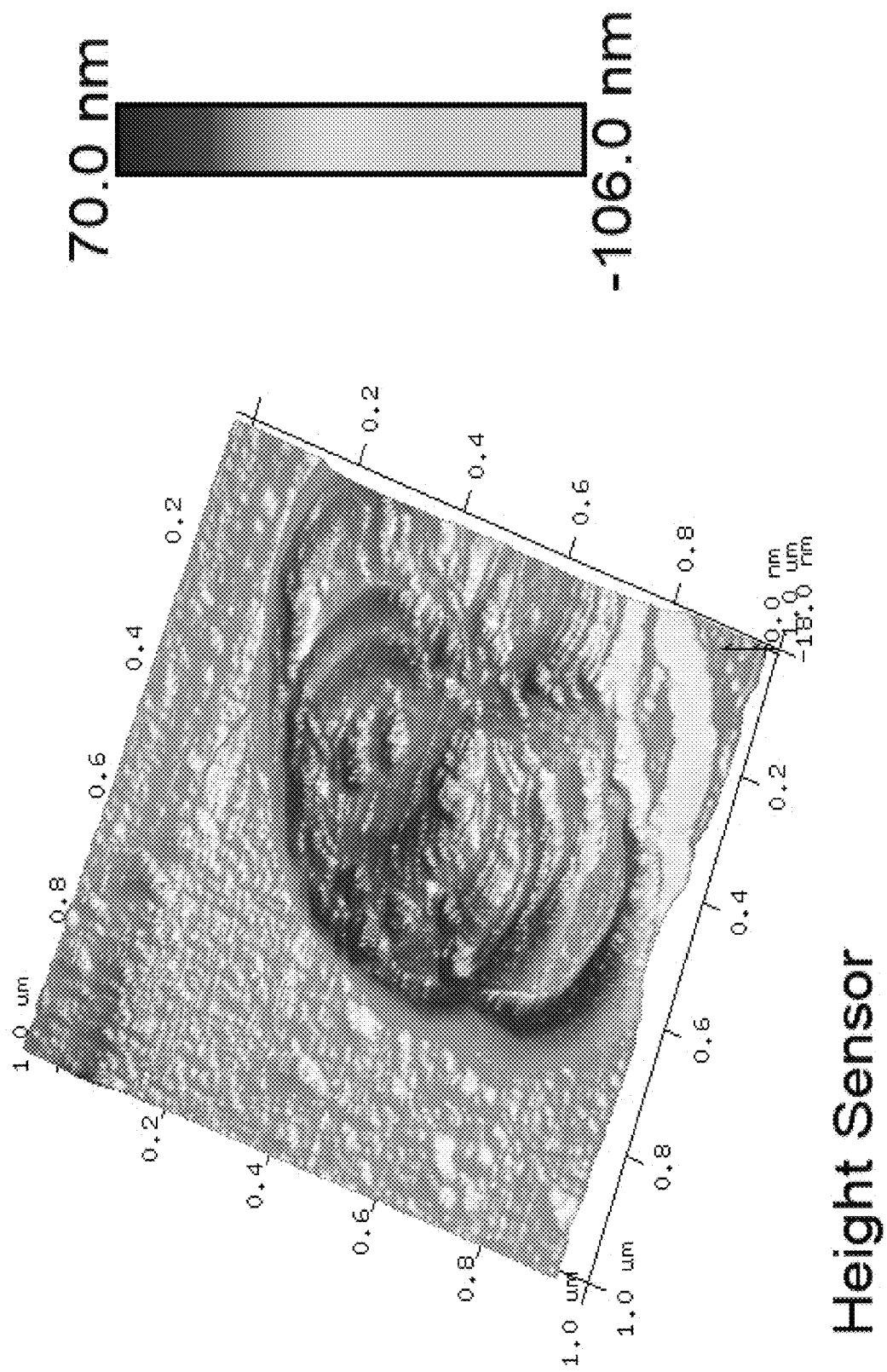
FIG. 3C depicts the 3D AFM image from the bird's view.
Figure 3D:
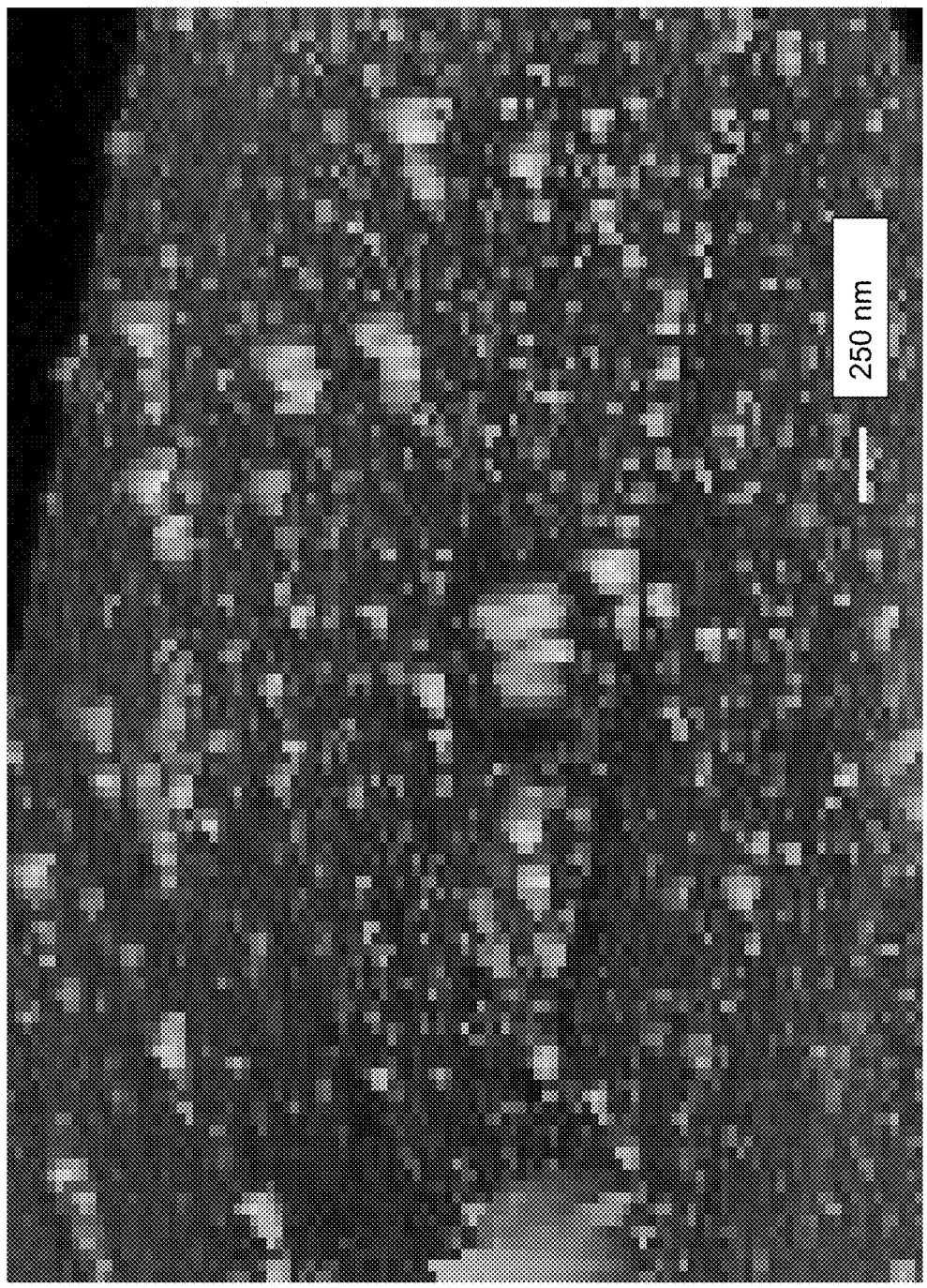
FIG. 3D depicts the enlarged image in 0.9×0.9 µm² shown in the flat area in FIG. 3I.
Figure 3E:
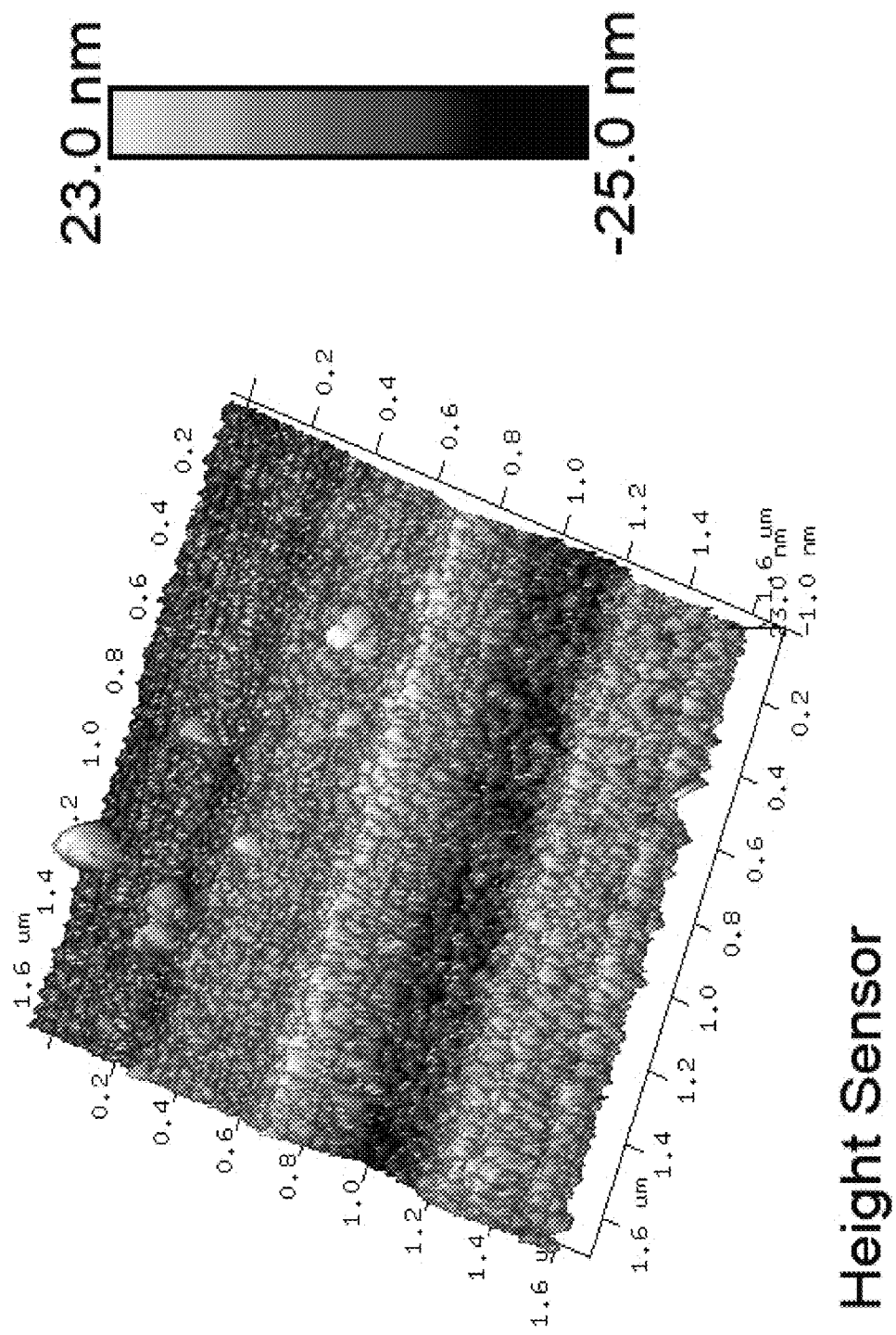
FIG. 3E depicts the alternative band deep-band flat formation of the membrane which promotes the Cooper-pair electron cloud mobility in 1.6×1.6 µm².
Figure 3G:
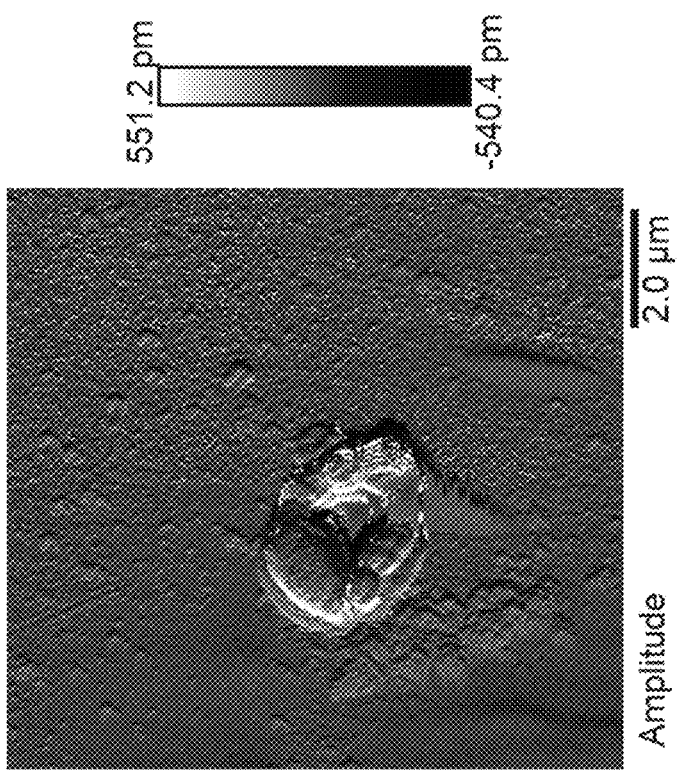
FIG. 3G depicts the top view in an amplitude mode of the AFM image of the large single porous biomimetic HSP60 structure.
Figure 3F:
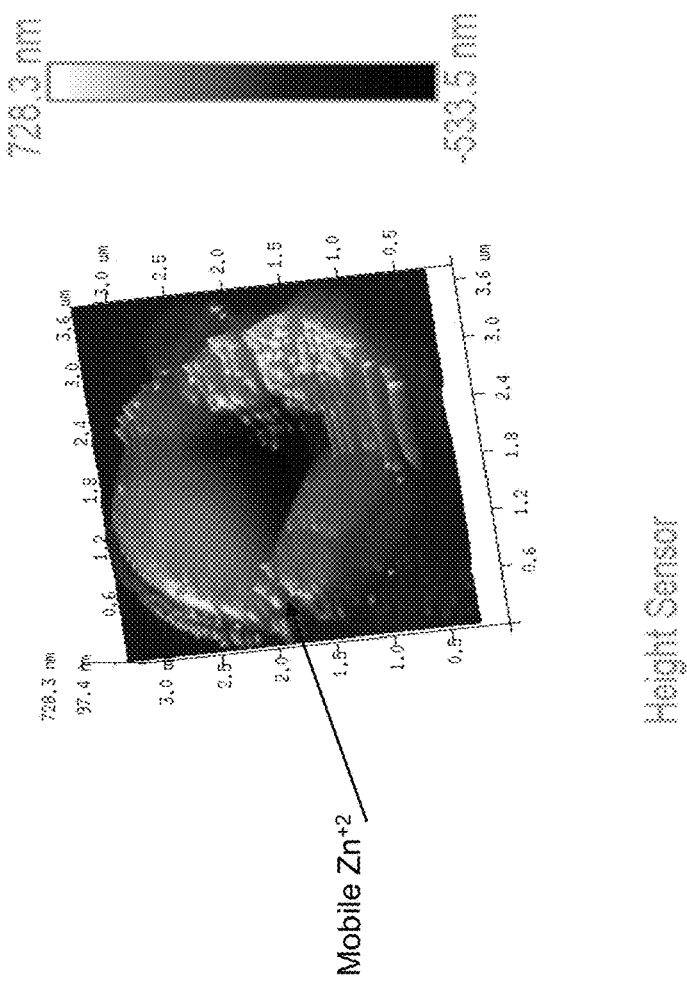
FIG. 3F depicts the enlarged 2D AFM image at high sensor mode in a top view of the biomimetic Heat Shock Protein (HSP) 60 chaperone structure having 7 subunits as shown on the top. The arrow indicates the mobile zinc ions.
Figure 3H:
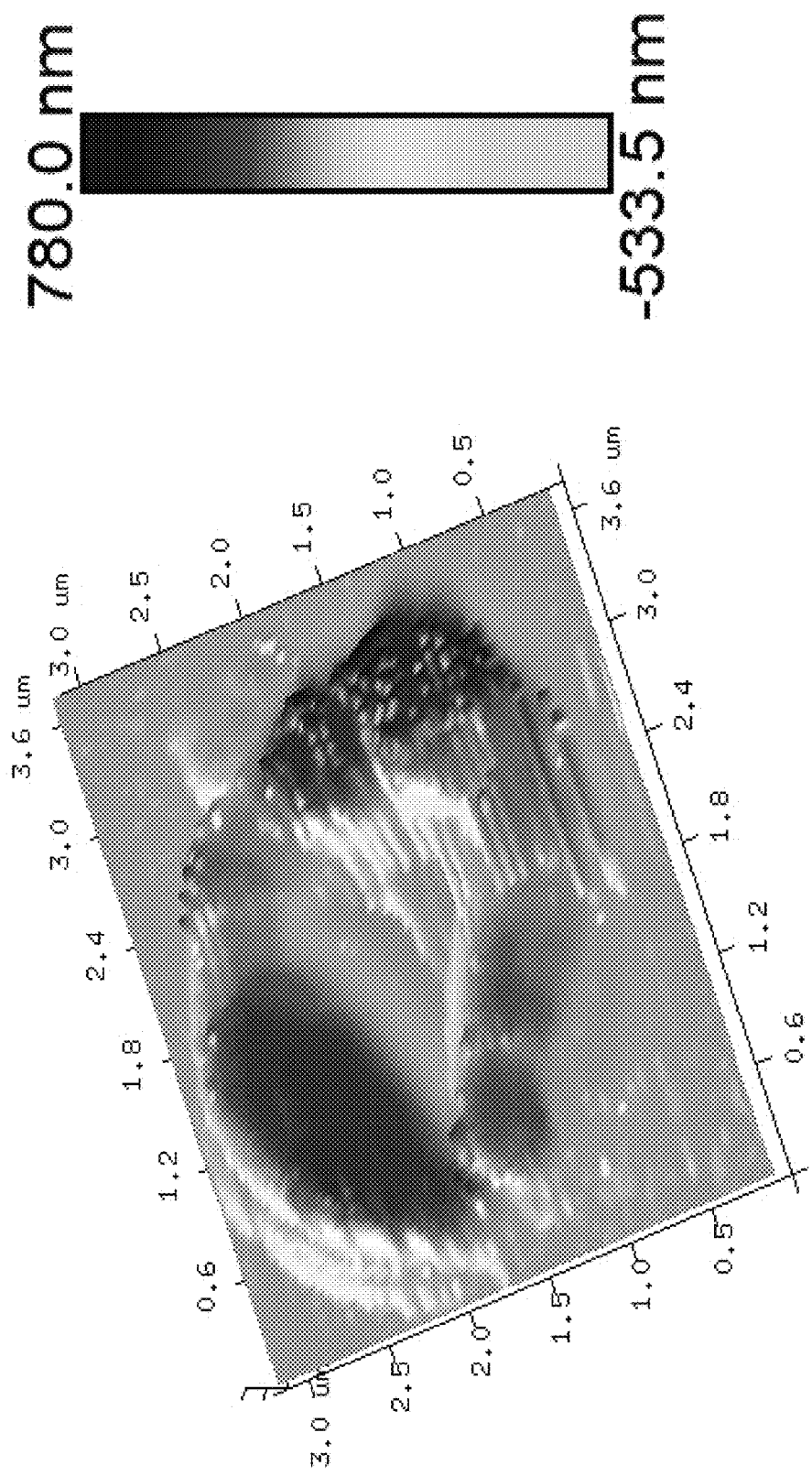
FIG. 3H depicts the side view of the 3D AFM image in high sensor mode for the single porous structure in 3×3.6 µm².
Figure 3I:
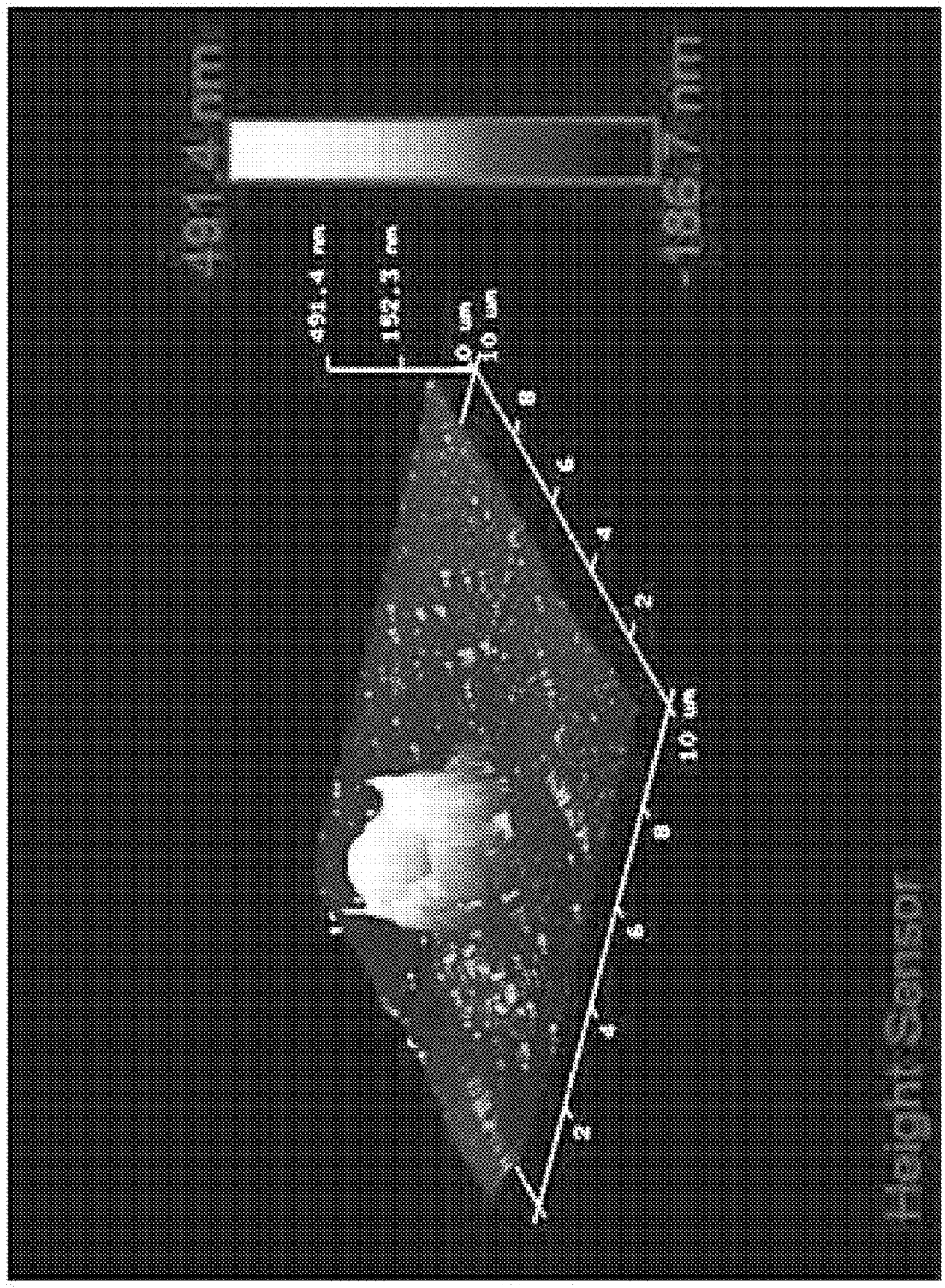
FIG. 3I depicts the 3D AFM image of the tall cylinder structure of the biomimetic HSP60 in 10×10 µm².

FIG. 3B depicts the cross-section analysis of the AFM membrane image. FIG. 3C depicts the 3D AFM image from the bird's view. FIG. 3D depicts the enlarged image in 0.9×0.9 µm² shown in the flat area in FIG. 3I. The Friedel-oscillation observed as the moving flames surrounded the zinc atoms, while the Cooper pairs moved toward the same direction and the superlattice matrix was very orderly arranged on the surface of the FIG. 3D. FIG. 3E depicts the alternative arrangement between the valley band and the flat band on the membrane which promotes the Cooper-pair electron cloud mobility in 1.6×1.6 µm². FIG. 3F depicts the enlarged 2D AFM image at high sensor mode in a top view of the biomimetic Heat Shock Protein (HSP) 60 chaperone structure having 7 subunits as shown on the top. The arrow indicates the mobile zinc ions. FIG. 3G depicts the top view in an amplitude mode of the AFM image of the large single porous biomimetic HSP60 structure. FIG. 3H depicts the side view of the 3D AFM image in high sensor mode for the single porous structure in 3×3.6 µm². FIG. 3I depicts the 3D AFM image of the tall cylinder structure in a size of 1.3-1.5 Lm diameter and 491 nm in height of the biomimetic HSP60 in 10×10 µm².

EXAMPLE 3

Direct Electron Relay (DER) Model Based on a Cylinder Cage-Like Structured Polymer Network FIG. 4A illustrates the Direct Electron-relay (DER) art model made by a cage-structured polymer network between the zinc ions from the activated biomimetic MMP-2, by elimination of the cysteine group from the polymer mixture of bM-β-DMCD/TCD/PEG/PVP/ZnCl₂ before deposited on the gold chip, and the mM-β-DMCD (short names as MCD) in Tris/HCl buffer. Zinc ions coordinated with three imidazole groups (two from the bM-β-DMCD and one from the MCD), and either with the COO— of TCD, or OH— group from the cyclodextrin, or from water. Furthermore, all other hydrogen bonding, hydrophobic interaction, and the p-p interaction between the functional groups inside the cavity induced the DER force evidenced as the Cooper pair electron freely moving toward the same direction shown in FIG. 3D and the cylinder cage structure was shown from FIG. 3F to FIG. 3I.

FIG. 4B depicts the art model when ATP interacts with the cylinder polymer network molecules that form an enhanced DER. This effect has enabled ATP to play a role to transform a memristive/meminductive sensor to a superconductor at a scan rate ≥60 Hz with an ATP concentration higher than 400 aM at the zero-bias potential.

EXAMPLE 4

The JJ Characteristics

The hallmarks of the JJ characteristics are (1) at a DC voltage=0, a supercurrent $$I_s = I_c \sin(\Delta\varphi) \quad (1)$$

$I_c$ is critical current, $\Delta\varphi$ is the phase difference between the waves of two superconductors, which appears at the DC Josephson junction; (2) at a finite DC voltage, the phase of the supercurrent has changed as a function of time that caused oscillating at the AC Josephson Junction, which is proportional to $2\ eV_{DC}$, i.e., $$\partial\varphi/\partial t = (2e/h)V_{DC} \quad (2)[28].$$

Here the Planck constant=h/2π (1.055×10⁻³⁴ Js). Scan frequency affects i-V curves shown in FIG. 5A for Sensor 1 is different from that of Sensor 2 in FIG. 6, both figures were working in the Tris/mono-substituted imidazole dimethyl-β-cyclodextrin (mM-β-DMCD), in short, MCD control media over 1 Hz to 25 kHz. Sensor 1 demonstrated a memristive behavior with a hysteresis point at zero V and zero current at 60 Hz, but it had no superconductivity through all the curves, which indicates the heating procedure damaged the superlattice structure leading to a poor Cooper pair formation. In contrast, Sensor 2 demonstrated perfect memristive behaves at 60 Hz and also showed the superconductivity at zero-bias potential over 5 kHz to 25 kHz as shown in FIG. 6. This fact showed as long as the Cooper pair formation, the superconductivity can be expected. The sine waves oscillated in the high scan frequency are observed.

EXAMPLE 5

Superconductivity with Super-Positioning

Because Sensor 1 lacks Friedel-oscillation due to the heating process for eliminating the cysteine group, without any superconductivity regardless with or without ATP in the Tris media as shown in FIG. 5A (without ATP) and 5B (with ATP) over a wide range of scan rate. Scan frequency effects on the Shapiro step voltage in the sine waves of Sensor 2 over 5 kHz to 25 kHz, under external magnetic field=0 condition, was observed as shown in the i-V curves in FIG. 6, FIG. 7, and FIG. 8 for without and with ATP under 60 and 10 kHz scan rate, respectively. The superlattice quantum bit's superposition states were seen between state "1" at v=0, I>0; "−1" state at v=0, I<0 and state "0" at v=0, I=0 at zero bias in FIG. 7 and FIG. 8.

EXAMPLE 7

Sensing ATP by Sensor 2 Using the CV Method and ATP Promotes Super Conductivity

FIG. 5B depicts the Direct Electron Transfer ($DET_{red}$) peak current increased exponentially for Sensor 1 as the ATP concentration increased from 40 fM to 60 nM compared with the control having 66.5, 146, 3048.7, and 4664-fold increase in four levels, respectively at 60 Hz scan rate. FIG. 6 shows scan rate impacts on Sensor 2's i-V curves over scan rate from 1 Hz to 25 kHz in the Tris/HCl/MCD control media.

FIG. 7 shows Sensor 2's sine or cosine wave peak superconducting current intensity increased or decreased exponentially for the forwarding scan and backward scan, respectively, over ATP concentrations from Panl B, 400 aM; Panel C: ATP 400 fM; Panel D: ATP 200 pM; Panel E: ATP 200 nM; Panel F: ATP 2 μM. at zero-bias at the same scan rate of 60 Hz compared with the controls in FIG. 6. We observed that a 25 aM ATP concentration is not enough to turn memristive to superconductivity shown in Panel A. The superposition characteristics were shown also as an example labeled in Panel F. The exponential increase of the superconducting current vs. ATP concentrations over 400 aM to 2 μM for the forward scan against the backward scan, which is in an exponential decay, were shown in FIG. 9. At a high scan rate of 10 kHz, both the forward and the backward scan's supercurrent at zero-bias increased non-linearly from 200 fM till near 1 μM, both currents is dropped drastically as shown in FIG. 10. FIG. 10 depicts the supercurrent vs. ATP concentration curves of the $DET_{red}$ and $DET_{ox}$ peaks at the zero-bias over ATP concentration ranges from 200 fM to 200 μM. Data was obtained according to the figures from FIGS. 8A to 8I.

EXAMPLE 9

ATP Induces Phase Change in Detail Presented in Sensor 2

Above Section we discovered ATP promoted superconductivity at an appropriate concentration and scan rate in the Tris buffer, now this Section we explain the invention of the technology on Sensor 2 and discovered the ATP's other role which is for inducing a phase change as shown in FIG. 11 for 10 consecutive scans at 60 Hz. The curves from Panel A are with an ATP concentration of 400 fM; Panel B with ATP 200 μM; Panel C with ATP 200 nM, and Panel D with ATP 2.0 μM, respectively. The phases of the i-V curves were constantly changing at a fixed scan rate, but the ATP concentration was increased.

FIG. 12A depicts the i-V curves of a 25 aM low concentration ATP in consecutive 5 scan cycles at a scan rate of 60 Hz compared with the control of Sensor 2. There was no phase change occurred, and the hysteresis curves are seen through the 5 consecutive scans. FIG. 12B depicts when concentration increased to 400 fM, in the consecutive 9 scan cycles of the same scan rate, we observed the cross-point moved away from the origin, and the i-V curves having the degree of superconductivity at zero-bias, and companies with a phase change occurred compared with the control. FIG. 12C also depicts a similar trend when ATP concentration increased to 200 nM ATP concentrations, Sensor 2 shows the phase changes and superconducting current.

EXAMPLE 10

The 3D Quantum Conducting Map in the Multiple-Variable Study

Quantum computing is computing using quantum-mechanical phenomena, such as superposition and entanglement [28]. Superconducting flux qubit has two states that can be effectively separated from the other states and is the basic building block of quantum computers. Current DC or RF superconducting SQUID are made in advance for a faster switch time; however, hundreds of MHz electromagnetic field applied onto a tank circuit coupled to the SQUID is needed for the system to work under cryogenic conditions [29-31]. The RF-SQUID consists of a superconducting ring of inductance L interrupted by a JJ, the potential energy of the SQUID and the Hamiltonian equations are given by $$U(\Phi)=(\Phi-\Phi_c)^2/2L-E_J\cos(2\pi\Phi/\Phi_0) \quad (3)[28]$$

$$H=Q^2/2C+(\Phi-\Phi_c)^2/2L-E_J\cos(2\pi\Phi/\Phi_0) \quad (4)[28]$$

$\Phi_c$ is the applied magnetic flux penetrating the SQUID ring, $\Phi$ is the total magnetic flux threading the SQUID ring, L is the inductance, $E_J$ represents the Josephson coupling energy, and $\Phi_0$ is the superconducting magnetic flux quantum, Q is the charge on junction's shunt capacitance satisfying $[\Phi, Q]=ih/2\pi$, while h is the Planck constant.

Stern's group reported the observation of Majorana bound states of Josephson vortices in topological superconductors, and the equations of three types of energy contributions to the Josephson vortices in a long circular junction in a Sine-Gordon system was published [32]. The Josephson junction energy was from the Cooper pair, the magnetic energy was from the inductivity of the circular vortex, and the charge energy was from the SIS quantum capacitor-like device [32-33]. Our group reported using a 3D dynamic map method, to elucidate the multiple-variables between the component energies contributing to the superconductivity of the vortex array system at room temperature without external magnetic field applied. Our experimental data were shown on the i-V curves and the AFM structure of the superlattice array. The modified Sine-Gordon system energy for our d-wave vortex array is:

$$E^n_{JJA}=(\frac{1}{2})C^{-1}_i(Q-en_{1\ldots i})^2 \quad (5)$$

$$E^n_L=(\frac{1}{2})\mu_0 N^2_{n=1\ldots u}\cdot A\cdot L^{-1}_{n=1\ldots i}I^2_{n=1\ldots i} \quad (6)$$

where $E^n_{jjA}$ is the charge energy of Josephson Junction arrays at n=1 . . . i; Q is the charge, C is the total capacitance at n=1 . . . i, en is the n quantum particles at 1 . . . i data point with energy periodic in h/e for Josephson effect for d-wave [34]; $E^n_L$ is the Inductive energy induced by the circular toroidal array. N is the turning number around the toroidal porous at n=1 . . . i, A is the cross-sectional area of the porous, L is the length of the wending, $\mu_0$ is the magnetic permeability constant in free space; I is current. The toroidal arrays are in series connected. A recent publication regarding our FFTJJ multiple-variable study results in 3D dynamic maps was presented in the literature [34]. In this invention, the multiple variables, such as the ATP concentration and the applied potential effect on the quantum conductance were studied through the 3D mapping method without decomposing the superconducting energy into several components.

FIG. 13 depicts the 3D dynamic map of the relationships over 5-level ATP concentrations from 0.2 μM to 2.0 μM over the potential range between −40 mV to +40 mV to illustrate the relationship among ATP concentrations, zero-bias potential, and the differential quantum conductance using 10 kHz scan rate forwarding scan data. From the map, the quantum conductance values are correlating with the ATP concentrations at zero bias, except at a higher concentration near 1.0 μM, it was dropped.

EXAMPLE 11

Quantitation of ATP in Biological Specimens

The Chronoamperometric Method (CA) was Measured by Sensor 1.

FIG. 14 depicts Sensor 1's current vs. time over ATP concentrations over 100 aM to 400 nM compared with the control in pH 7.8 Tris/HCl/MCD solution. FIG. 15 depicts the lower-end concentration curves. Inserts are enlarged views for lower end concentration compared with controls. Inserts are the enlarged view of the curves at the lower concentration compared with the control. FIG. 16 in Panel A depicts the regression calibration curve of current density vs. ATP concentrations in a logarithm scale for the x-axe and the y-axe (9 levels, n=27 over 100 aM to 400 nM) with the regression equation (y log scale)Y=1.9+0.57*(log scale)χ, r=0.996, $S_{Y/\chi}$=0.16, p<0.0001. In the inversion of the equation, 0.57 is the power of the χ, and 1.9 is the intercept from the log-log plot. Hence the inversed equation is F(x)=79×$^{0.57}$. FIG. 16 Panel B depicts Sensor 1's calibration curve over a linear range of 400 fM to 170 nM (7 levels, n=21) with the regression equation y=65.4+13.4x, r=0.997, Sy/x=65, p<0.0001. The Detection of Limits (DOL) of 0.56 fM over the analytical range 100 aM-400 nM with a relative Pooled Standard Deviation (RPSD) value of 0.9% (n=30).

EXAMPLE 12

The Open Circuit Potential Method (OPO)

Sensor 2's strong superconductivity has enabled the device to direct real-time monitor energy change under open circuit potential, under a reagent-free, antibody-free condition. FIG. 17 depicts the voltage curves exponentially increasing as the ATP concentration increase compared with the control in the buffer media. FIG. 18 depicts the non-linear calibration curve of voltage vs. concentrations over the range of 25 aM to 400 μM. FIG. 19 shows a plot for high-end ATP concentration with spontaneous voltage curves as the time (600 s) over 0.8 nM (a) to 2 μM (d). FIG. 20 shows the calibration curve over the higher ATP concentration range from 0.8 nM to 2 μM.

EXAMPLE 13

The Double Step Chronopotentialmetry Method (DSCPO) by Sensor 2

The ATP concentrations also can be detected in several seconds using the DSCPO method and setting the fixed current as ±10 nA, and each step 4s with a data rate of 1 kHz. FIG. 21 depicts Sensor 2's voltage vs. time (each step 4s) curves by the Double-step Chronopotentialmetry (DSCPO) method in the presence of various ATP concentrations from 25 aM to 400 nM in the Tris/HCl/MCD buffer compared with the control. Each sample run triplicates. The curves show a positive correlation between the voltage intensity and the ATP concentrations in 7 levels compared with the lowest voltage from the control. FIG. 22A depicts the calibration curve of the normalized action potential divided by the mean signal vs. ATP concentrations over 100 aM to 200 nM. The relative pooled standard deviation (RPSD) is 0.24%. The linear semi-log plot gave an equation of yscale (Y)=A+B*xscale(X) with A=0.37 and B=0.06, r=0.992, n=18, $S_{y/log\ x}$=0.027, p<0.0001. The DOL found from this plot is 46 aM. FIG. 22B depicts the low-end ATP calibration curve from ATP 25 aM to 400 aM in the Action potential results of the DER peaks after subtracting the background signals with an RPSD error of 1.3% with the signal increase rate of 0.016V/aM. The DOL result is 2 aM. FIG. 22C depicts the semi-log plot of the absolute normalized resting potential vs. ATP concentrations under the same experimental conditions as FIG. 22A having a power 4.39 indicated the resting potential effects on ATP concentration lower than 100 aM, which is dominate than that of the action potential effect.

EXAMPLE 14

Accuracy and Imprecision

The USDA-certified organic milk for infants was compared with human milk (Lee Biosolutions, MO) without prior sample preparation. Human milk was collected from normal subjects who breastfeed 1 month-old newborn, each sample run triplicates.

Methods validations were studied through the recovery experiments using fresh human milk and USDA-certified organic milk for infants as controls compared with spiked 100 aM and 60 nM ATP and with or without low and high-level LPS challenges by the OPO method against each one's standards and the controls. The accuracy recoveries were 94±0.14% and 91±0.16% at 100 aM and 60 nM ATP for the human milk samples compared with organic milk samples of 85±0.2% and 79%±0.2%, respectively using the OPO method is traced back to the Tris standard control. The human mike control and the organic milk control samples have an agreement related to the Tris/HCl/MCD buffer sample controls (each type sample run triplicates) are 94.0±0.14% and 95.5±0.2%, respectively. The 5% difference is believed due to the artificial chaperone cage effect on the proteins of the milk, which is to lead the landscape free energy down to the lowest for a right folding [29-30]. After correcting this effect, human milk's recovery in the two levels' ATP challenges is 98±0.14% and 95±0.16%; the organic milk recoveries are 90.5±0.2% and 84.5±0.2%, respectively. The data implies the chaperoning effect has more impact on organic milk than that on human milk. In the two levels' LPS challenges (100 ag/mL, 60 ng/mL), the recovery results are 96±0.16% and 105±0.14% vs. 105.5±0.28% and 95±0.19% for human milk and organic milk, respectively.

Point accuracy and imprecision were studied through the recovery experiments using spiked human milk and the USDA-certified organic milk samples against the control samples with 2 levels of ATP concentrations at 100 aM and 60 nM, respectively. We compared the measured results with the calibration curve after subtraction of the voltage values from control samples using sensor 2 as shown in FIG. 22D of Table 1. We also studied the LPS effects on the recovery at 10 fg/mL and 90 fg/mL, respectively under a fixed ATP concentration of 60 nM. The results show the recoveries using human milk and organic milk samples with the voltage method are higher than 96% with an imprecision error less than or equal to 2% at the 100 aM and 60 nM levels ATP compared with the controls, respectively without LPS challenge. Using two levels of LPS challenges with the fixed ATP 60 nM, the recoveries are 103±0.8%, and 103±0.7% for human milk samples compared with the spiked controls at the same level in the buffer; using organic milk samples, the recoveries are 97±1%, 18.8±0.3% at 10 fg/mL LPS and 90 fg/mL LPS, respectively traced back to the spiked controls at the same level in the buffer. These results showed organic cow milk samples are vulnerable to the LPS attack at higher-level 90 fg/mL, which caused an unacceptable result in recovery, but the human milk samples demonstrated immunological advantage with 100% recovery with two levels of LPS challenges even under 60 nM ATP concentration.

The CA method was also used to access the accuracy and imprecision. Human milk control samples against the standard control samples in the Tris/HCl/MCD buffer found no specimen interference having 101±6% traceable to the standards; In the presence of 30 fM ATP spiked in the human milk samples, i.e., the final ATP concentration is 30 fM in the sample, the recovery results are 100.0±7%; However, when 60 nM ATP presents in the human milk samples, due to the immunological property, human milk samples eliminated all the ATP's effect, led to no signals were measurable; In the presence of 30 fM ATP, under a 10 fg/mL LPS challenge of the human milk samples, the recovery results are 100±10%; Under 30 fM ATP, using a 90 fg/mL LPS challenge, the human milk samples produce 3-fold high signal intensity, For comparison, the organic milk control samples were found to have a 21% of HSP 60-like chaperone interference for trace back to the standard control samples with 79±2.6%; in the Tris/HCl/MCD buffer; After correcting the interference, in the presence of 30 fM ATP spiked in the organic milk samples, the recovery results are 100.0±4.4%; when 60 nM ATP presents in the organic milk samples, the recovery results are 102.3±0.02%; In the presence of 30 fM ATP, under a 10 fg/mL LPS challenge of the organic samples, the recovery results are 49±0.2%; Using a 90 fg/mL LPS challenge to the organic milk samples, the recovery results are 130±3.6%.

EXAMPLE 15

Applications for Defining the Transformational Immunomodulant Between the Anti-Inflammatory and the Pro-Inflammatory Status We primarily suggest the turning point of the ATP concentration from anti-inflammatory to pro-inflammatory for a "healthy" Biomimetic MMP-2/HSP60 sensor 2 in the extracellular environment is higher than 800 nM. FIG. 23 further shows a contour map relationship between the ATP concentration (as the y-axis), the applied potential (as the x-axis), and the quantum conductance (as Z-axis). It was observed that the range between the highest quantum conductance values at zero bias is associated with the ATP concentration between 200 fM to 800 nM, so we define this range as having the Physiological High-Frequency Oscillation (Phy-HFO) as the "Anti-inflammatory" range; when concentration higher than 800 nM, the quantum conductance values are reduced, and this range was defined as the "Pro-inflammatory" in the extracellular ATP concentration range at 10 kHz. Because Sensor 1 can be viewed as a "Mutated" or "Stressful" Biomimetic MMP-2/HSP60 model as far as the capability to promote the Cooper-pair electrons' concerns, was greatly diminished as shown in the AFM image FIG. 2B, hence it was shown Sensor 1 neither have superconducting peaks in the presence of ATP in the buffer media in 60 i-z and 10 kHz scan rate, respectively.

EXAMPLE 16

Applications in Defining ATP Concentration Ranges Effecting on Cell Reversible Membrane Potential (RMP) and its Ratio Between Action Potential and Resting Potential It is a well-recognized phenomenon that cancer cells have abnormal cell membrane potential [35-38]. Biologists measure cell membrane action and resting potentials with burdensome instrumentation and time-consuming procedures. A recent report shows breast cancer cell division caused a membrane potential increase [38] due to variations in ion channel expression. Because the normal cell membrane action potential is 58 mV, and −70 mV is for the resting potential [39], the small signals are very easily buried in the background noises [40] that can cause problems for pediatric neurologists and intensive care unit doctors who need strong signals to monitor and diagnose the neonatal neurological diseases [40]. The consequences of human cancers, trauma brain injury (TBI) and other diseases are not being able to maintain mitochondrial cells' reversible membrane potential (RMP) and unable to maintain the normal membrane's potential ratio between the action potential and the resting potentials [35-44]. Our group first used the biological marker of the action/resting potential ratio to monitor the treatment of triple-negative breast cancer and the brain cancer prognosis in a 3D heat release map [41-44]. There are very few, if any, use the ratio of action/resting potential as a biomarker to monitor and define the ATP concentration ranges, that transform from anti-inflammation to pro-inflammation in the presence of bacterial toxins under a well-controlled system without any sample processing, no labeling and no tracers were used. FIG. 24 shows the cell RMIP voltage (after subtracting the control) is not depending upon the ATP concentrations between the range from 100 aM to 800 nM with a power of 0.013, which means the cell voltage increase rate is only 1.3% of the ATP concentration increase rate, hence this range is the "safe zone" confirmed by FIG. 10 using the 3D map method based on the CV data. However, we found concentrations lower than 100 aM and higher than 800 nM the cell RMP cannot keep constant, either lower than the normal average cell voltage, or 10, 20-fold higher than the normal average cell voltage, therefore, we define this range as the pro-inflammatory toxin range, for contrast, the "safe zone" range was defined as the anti-inflammatory toxin range.

FIG. 25 further shows the extracellular ATP concentration range effects on the ratio of the cell action potential vs. resting potential. The results showed a concentration lower than 100 aM or higher than 400 nM will lead to a ratio of action vs. resting potential either significantly lower or significantly higher than the normal ratio range, which is between 0.7 to around 1.0 [45-50]. Our prior works revealed that living cancer cells can lead to an abnormal ratio up to 3, 10 to 100-fold higher than this range according to the nature of cancer and the stage of the cancer are in. Even FIG. 24 reveals the total cell voltage at 800 nM is in the "safe zone" with respect to the energy concerns, but clinically, the ratio value in FIG. 25 further revealed the 800 nM ATP concentration led to a 10-fold higher than the normal ratio range, hence in FIG. 25 we excluded the 800 nM points. The ratio vs. concentration curve has a power of 0.08 which means the ratio increase rate is 8% of the concentration rate increase having a CV value±4.5% error in the normal range was demonstrated.

EXAMPLE 17

Applications in Assessing Human Milk Immunological Advantage in Preventing Extracellular ATP Hydrolyzation Assessing human milk's immunological advantage in preventing extracellular ATP hydrolyzation is important. Our study was conducted through the CV method using Sensor 1 because we knew Sensor 1 lacks Copper-pair electrons, and we used the human milk samples compared with the certified organic milk samples for infants under the same experimental conditions. FIG. 26, Left Panel shows the extracellular hydrolysis $DET_{ox}$ curves (also called the memristive peak) happened in the presence of spiked 60 nM ATP (final concentration), which caused a 9-fold increase of the peak current at 700 mV compared with the organic milk negative control. There is an unknown peak observed in the organic control milk sample located at 20 mV, and the peak was the 2.8-fold increase of the amplitude when ATP presences. In contrast, FIG. 26 in the Right Panel shows the buffer control sample of the CV curve has no such unknown peak at 20 mV. There is a current increase for the $DET_{ox}$ peak at 700 mV of more than 173-fold in the presence of 60 nM ATP compared with the control, and the $DET_{red}$ peak intensity also increased 150-fold in the presence of ATP compared with the control buffer sample. The $DET_{ox}$ has a first-order ATP hydrolysis rate of $5.92 \times 10^3$/s by plotting the peak currents vs. scan cycles (each cycle is 53.33 s) as shown in FIG. 27. The top Panel curve is for the DETred peak current vs. scan cycles; the bottom Panel curve is for the $DET_{ox}$ peak current vs. scan cycles.

Human milk samples communicated with the "mutated" HSP60 membrane on the same Sensor 1 having a different manner compared with the organic cow milk samples. FIG. 28A, FIG. 28B, FIG. 28C and FIG. 28D depict the human milk samples under the impact of 60 nM ATP concentration in 4 scan cycles (2 more cycles curves did not show) compared with the human milk controls using Sensor 1 at 60 Hz. The nodes, the super-positioning, and the phase change at the zero-bias were observed, and there was no ATP hydrolysis signature peak observed, and there was no unknown DET reduction peak noticed. FIG. 29 shows an alternative up and down peak superconducting current vs. scan cycles for the forward and backward scan, respectively. The human milk samples have "eyes" that can see the danger and purposely avoiding communicate with the ATP molecules because the human milk contains living microbiota, in which the HSP60 and ZnT chaperonin proteins in the extracellular play a role in the guardian's protection. FIG. 30 shows the overlapping curves of the control human milk sample in 6 consecutive scans vs. the milk sample with 60 nM ATP. The peak magnitude kept the same, but the phase change is constantly happening with or without ATP, that indicates human milk promotes an orderly electromagnetic energy stored in the cell for enhancing the brain development and memory caused by the mem inductivity through the Josephson junctions, in which are advantages compared with the "chaos" electromagnetic energy acquired from Alzheimer's 0-amyloidal accumulation [51-54].

EXAMPLE 18

Experimental

Sensor 1 has an activated biomimetic MMP-2 membrane by a heating method at 80° C. for 5 minutes using the innate biomimetic MMIP-2 membrane fabricated based on a published procedure [34]. Sensor 2 was also in a state of activation of biomimetic MMP-2 by a direct deposited method with compositions of TCD, PEG, PVP, bM-3-DMCD, and embedded zinc chloride on gold chips with appropriate proportions at 37° C. for 96 hours. The USDA-certified organic milk for infants was compared with human milk (Lee Biosolutions, MO) without prior sample preparation. Human milk was collected from normal subjects who breastfeed 1-month-old newborns, and each sample run triplicates.

The morphology of the AU/SAM was characterized using an Atomic Force Microscope (AFM) (model Dimension Edge AFM, Bruker, MA). Data was collected in Tapping-Mode using silicon probes with a 5-10 nm tip radius and –300 kHz resonance frequency (Probe mode TESPA-V2, Bruker, MA).

EXAMPLE 19

Conclusions and Discussions

A multiple-functioning superconductive device was invented based on Toroidal Josephson Junction (FFTJJ) array with a 3D-cage structure self-assembled organo-metallic superlattice membrane. The device not only mimics the structure and function of an activated Matrix Metalloproteinase-2 (MMP-2) protein, but also mimics the cylinder structure of the Heat Shock Protein (HSP60) protein, that works at room temperature under a normal atmosphere, and without external electromagnetic power applied. The device enabled direct rapid real-time monitoring of atto-molarity concentration ATP in biological specimens and was able to define the anti-inflammatory and pro-inflammatory status revealing a transitional range of ATP concentration under antibody-free, tracer-free, and label-free conditions.

What is claimed is:

1. A multiple-functioning superconductive device comprising:
   (a) an electrode has an organo-metallic superconductive membrane having arrays of 3D-nanocage structure;
   (b) wherein the 3D-nanocage structure comprising a direct electron-relay comprising of a biomimetic matrix metalloproteinase-2 (MMP-2) membrane and a media comprising of imidazole-modified cyclodextrin, and ATP formed chelating coordinating bounds, forming a long-range direct electron relay (DER) chain; and
   (c) wherein the organo-metallic superconductive membrane comprising of Toroidal Josephson Junction (TJJ) array.

2. A multiple-functioning superconductive device according to claim 1, wherein the superconducting membrane has Friedel-oscillation.

3. A multiple-functioning superconductive device according to claim 1 further comprising of multiple-layer ring structure in $0.734 \times 0.734$ μm² membrane according to Atomic Force Microscopy images mimicking cation-diffusive facilitator (CDF) protein YiiP of *E. coli* effluxion zinc ions from a cellular membrane, and mimics function and structure of the active MMIP-2 protein.

4. A multiple-functioning superconductive device according to claim 1, further comprising of direct rapid real-time monitored atto-molarity concentration ATP in biological specimens having point accuracy higher than 96% with imprecision errors less than or equals to 2% at a 100 aM and 60 nM ATP concentration levels, compared with the controls, respectively using a Double-step Chronopotentiometry (DSCPO), i.e., voltage method.

5. A multiple-functioning superconductive device according to claim 1, further comprising multiple-functioning for defining a transformational immunomodulant over an Anti-inflammatory of ATP concentration from 0.2 pM to 800 nM, and a Pro-inflammatory status in extracellular ATP concentration range higher than 800 nM was demonstrated at a scan rate of 10 kHz by a contour map analysis method with variables of ATP concentration, quantum conductance, and applied potential, especially at zero bias.

6. A multiple-functioning superconductive device according to claim 1, further comprising of multiple-functioning of monitoring the normality of a cell reversible membrane potential (RMP) for ATP concentration effect between 100 aM to 800 nM using a voltage method at ±10 nA with each potential step at 0.25 Hz.

7. A multiple-functioning superconductive device according to claim 1, further comprising of multiple-functioning of monitoring clinical normality of a ratio of a cell action potential vs. resting potential in ATP extracellular level over 100 aM to 400 nM is in a normal range of the ratio.

8. A multiple-functioning superconductive device according to claim 1, further comprising of multiple-functioning used for assessing milk immunological characteristics in preventing extracellular ATP hydrolyzation using biological specimens.

9. A multiple-functioning superconductive device according to claim 1, further comprising wherein a biomimetic activated MMP-2 superconductive device through a direct deposition method, direct quantitatively detects ATP in the range between 100 aM to 200 nM with a relative pooled standard deviation (RPSD) 0.24%, and a DOL value 46 aM using a voltage method.

10. A multiple-functioning superconductive device according to claim 1, further comprising of a quantum sensing function working under antibody-free, tracer-free, and label-free conditions at room temperature.

11. A multiple-functioning superconductive device according to claim 1, wherein the 3D-nanocage structure comprises of triacetyl-β-cyclodextrin (TCD), polyethylene glycol diglycidyl ether (PEG), poly(4-vinyl pyridine) (PVP), bis-substituted imidazole dimethyl-β-cyclodextrin (bM-β-DMCD), and zinc ions affixed on the surface of the electrode by cross-linking with appropriate propositions at 37° C. and 96 hours.

12. A multiple-functioning superconductive device according to claim 2, wherein the Friedel-oscillation is due to Cooper-pairs hop through a Josephson toroidal junction barrier having superconductive/memristive/memcapacitive functions to enable quantum sensing.

13. A method of using a multiple-functioning superconductive device according to claim 12, the method comprising of using a cyclic voltammetry (CV) method direct measuring a superconducting current change at zero bias potential due to a biomarker participated in the DER chain comprising:
a) obtaining a biological sample which can be detected;
b) contacting the biological sample with the device comprising of superconductive/memristive/memcapacitive Josephson toroidal junction array quantum sensing functions (JTJAQS);
c) connecting one lead to the JTJAQS as a cathode and another lead to be an anode, and a reference electrode to be connected to a third lead at a fixed scan frequency setting;
d) setting up the applied potential range to be scanned crossing zero bias;
e) apply the electric potential;
f) measuring and recording a superconducting peak current change at zero bias in the presence of an analyte;
g) and comparing a result with that of a control sample without the presence of the analyte.

14. A method of using of a multiple-functioning superconductive device according to claim 12, the method comprising of direct measuring an intrinsic equilibrium energy change using an Open Circuit Potential (OPO) method in a specimen sample at real-time comprising:
(a) obtaining a biological sample that can be detected;
(b) contacting the sample with a device comprising of superconductive/memristive/memcapacitive Josephson toroidal junction array quantum sensing functions (JTJAQS);
(c) connecting the JTJAQS;
(d) setting up an appropriate time unit either in second or in minute to be measured;
(e) setting up data acquisition time interval;
(f) measuring and recording voltage change in the presence of an analyte;
(g) and comparing a result obtained from step f with that of a control sample without the presence of the analyte.

15. A multiple-functioning superconductive device according to claim 3, further comprising of a larger porous cylinder structure in $10.0 \times 10.0$ $\mu m^2$ membrane according to Atomic Force Microscopy images of mimicking a Heat Shock Protein (HSP60) with a 1.3-1.5 µm diameter ring at bottom and a height is 491 nm, which comprises seven subunits mimicking HSP60's subunits.

16. A multiple-functioning superconductive device according to claim 1, further comprising of a rapid and accurate hygiene monitoring function having high selectivity to ATP, but is not sensitive to interference from lipopolysaccharide (LPS) of *E. coli* over concentration range up to 90 fg/mL spiked in human milk samples with recovery accuracy 103±0.8% compared with controls.

\* \* \* \* \*